(12) United States Patent
Bhimavarapu et al.

(10) Patent No.: US 12,274,652 B2
(45) Date of Patent: Apr. 15, 2025

(54) EXERCISE DEVICE AND PATIENT SUPPORT APPARATUS

(71) Applicant: Stryker Corporation, Kalamazoo, MI (US)

(72) Inventors: Krishna Sandeep Bhimavarapu, Kalamazoo, MI (US); Celso Henrique Farnese Pires Pereira, Portage, MI (US); Jeffrey Kennedy, Kalamazoo, MI (US); Kaitlin Therese Konopacz, Lake Zurich, IL (US); Heather Sirianni, Aliso Vieso, CA (US)

(73) Assignee: Stryker Corporation, Portage, MI (US)

( * ) Notice: Subject to any disclaimer, the term of this patent is extended or adjusted under 35 U.S.C. 154(b) by 402 days.

(21) Appl. No.: 17/695,151

(22) Filed: Mar. 15, 2022

(65) Prior Publication Data
US 2022/0287897 A1     Sep. 15, 2022

Related U.S. Application Data

(60) Provisional application No. 63/161,175, filed on Mar. 15, 2021.

(51) Int. Cl.
*A61G 7/05* (2006.01)
*A63B 21/00* (2006.01)
(Continued)

(52) U.S. Cl.
CPC ............ *A61G 7/05* (2013.01); *A63B 21/0442* (2013.01); *A63B 21/0557* (2013.01);
(Continued)

(58) Field of Classification Search
CPC .................. A63B 22/0087; A63B 21/02–0557
See application file for complete search history.

(56) References Cited

U.S. PATENT DOCUMENTS

| | | | | |
|---|---|---|---|---|
| 2,340,666 A | * | 2/1944 | Johanson | A47C 20/022 5/651 |
| 5,673,447 A | * | 10/1997 | White | A47C 20/022 5/651 |

(Continued)

FOREIGN PATENT DOCUMENTS

| | | |
|---|---|---|
| WO | 9427544 | 12/1994 |
| WO | 2008052220 A3 | 5/2008 |

(Continued)

OTHER PUBLICATIONS

Stryker iBed Server v3.0 Installation/Configuration Manual, Feb. 2021.

*Primary Examiner* — Nyca T Nguyen
(74) *Attorney, Agent, or Firm* — Warner Norcross + Judd LLP

(57) ABSTRACT

An exercise device includes one or more connectors adapted to be releasably coupled to a patient support apparatus; a patient-contacting portion adapted to contact a portion of the patient's body and to be resistively moved between a first position and a second position; a first location transceiver; and a sensor adapted to automatically detect movement of the patient-contacting portion between the first and second positions. The exercise device may also include a wireless transceiver adapted to transmit movement data derived from the sensor to a recipient device. In some embodiments, the exercise device is part of a system that includes a patient support apparatus and a second location transceiver positioned thereon. The location transceivers allow a controller to determine if the exercise device is currently coupled to the patient support apparatus or not, and/or to automatically pair the exercise device to the patient support apparatus for wireless communication.

20 Claims, 8 Drawing Sheets

(51) Int. Cl.
*A63B 21/04* (2006.01)
*A63B 21/055* (2006.01)
*A63B 24/00* (2006.01)
*G16H 40/63* (2018.01)

(52) U.S. Cl.
CPC ...... *A63B 21/4034* (2015.10); *A63B 24/0062* (2013.01); *G16H 40/63* (2018.01); *A63B 2208/0252* (2013.01); *A63B 2220/17* (2013.01); *A63B 2220/40* (2013.01); *A63B 2220/803* (2013.01); *A63B 2225/50* (2013.01)

(56) References Cited

U.S. PATENT DOCUMENTS

| | | | |
|---|---|---|---|
| 7,852,208 B2 | 12/2010 | Collins, Jr. et al. | |
| 9,571,985 B2 | 2/2017 | Bottazzi et al. | |
| 9,788,151 B2 | 10/2017 | Duan et al. | |
| 9,999,375 B2 | 6/2018 | Hayes et al. | |
| 10,064,012 B1 | 8/2018 | Boston et al. | |
| 10,235,845 B2 | 3/2019 | Bhimavarapu et al. | |
| 10,257,063 B2 | 4/2019 | Bhimavarapu et al. | |
| 10,426,998 B1* | 10/2019 | McRee | A63B 21/023 |
| 10,456,309 B2 | 10/2019 | Constant et al. | |
| 10,486,646 B2 | 11/2019 | Ledvina et al. | |
| 10,608,699 B2 | 3/2020 | Nabki et al. | |
| 10,679,489 B2 | 6/2020 | Bodurka et al. | |
| 10,716,474 B2 | 7/2020 | Bodurka et al. | |
| 10,759,389 B2 | 9/2020 | Ledvina et al. | |
| 10,846,961 B2 | 11/2020 | de Perthuis et al. | |
| 11,019,195 B2 | 5/2021 | Ledvina et al. | |
| 11,026,067 B2 | 6/2021 | Martin et al. | |
| 11,082,809 B1 | 8/2021 | Burowski et al. | |
| 11,110,020 B2 | 9/2021 | Bodurka | |
| 11,153,810 B2 | 10/2021 | Yoon et al. | |
| 11,301,651 B2 | 4/2022 | Studerus et al. | |
| 11,343,645 B2 | 5/2022 | Yoon et al. | |
| 11,400,889 B2 | 8/2022 | Parthasarathi et al. | |
| 11,475,789 B2* | 10/2022 | Lagree | G09B 19/0038 |
| 11,623,126 B1* | 4/2023 | Lagree | A63B 21/4035 482/5 |
| 2002/0014951 A1 | 2/2002 | Kramer et al. | |
| 2012/0190503 A1* | 7/2012 | Shavit | A63B 24/0062 482/5 |
| 2012/0190505 A1* | 7/2012 | Shavit | G06F 3/017 482/8 |
| 2014/0094721 A1* | 4/2014 | Diallo | A63B 24/0087 601/5 |
| 2014/0276273 A1* | 9/2014 | Leismer | A63B 23/0405 601/49 |
| 2015/0290061 A1* | 10/2015 | Stafford | A63B 22/0089 5/600 |
| 2016/0038361 A1 | 2/2016 | Bhimavarapu et al. | |
| 2018/0099182 A1* | 4/2018 | Miettinen | A61B 5/681 |
| 2018/0280782 A1* | 10/2018 | Lagree | A63B 71/0619 |
| 2019/0008394 A1* | 1/2019 | Rao | A61B 5/1118 |
| 2019/0269967 A1* | 9/2019 | Thomas | A63B 21/00185 |
| 2020/0113518 A1* | 4/2020 | Mollohan | G06F 1/163 |
| 2020/0289888 A1* | 9/2020 | Neuman | A63B 22/0056 |
| 2021/0014677 A1 | 1/2021 | Han et al. | |
| 2021/0065885 A1 | 3/2021 | Receveur et al. | |
| 2021/0174268 A1* | 6/2021 | Levinson | G06Q 50/10 |
| 2021/0266710 A1 | 8/2021 | Martin et al. | |
| 2021/0360366 A1 | 11/2021 | Bailey et al. | |
| 2021/0400439 A1 | 12/2021 | Troester et al. | |
| 2022/0053292 A1 | 2/2022 | Hoff et al. | |
| 2022/0082676 A1 | 3/2022 | Lee et al. | |
| 2022/0137204 A1 | 5/2022 | Nguyen et al. | |
| 2022/0139133 A1 | 5/2022 | Schober et al. | |
| 2022/0266087 A1* | 8/2022 | Amoros | A63B 21/0428 |
| 2023/0105920 A1* | 4/2023 | Neuhaus | A63B 21/15 482/8 |

FOREIGN PATENT DOCUMENTS

| | | |
|---|---|---|
| WO | 2021228946 A1 | 11/2021 |
| WO | 2021236649 A1 | 11/2021 |

* cited by examiner

EXERCISE DEVICE AND PATIENT SUPPORT APPARATUS

CROSS-REFERENCE TO RELATED APPLICATIONS

This application claims priority to the following applications: U.S. provisional patent application Ser. No. 63/161,175 filed Mar. 15, 2021, by inventors Krishna Bhimavarapu et al. and entitled EXERCISE DEVICE AND PATIENT SUPPORT APPARATUS; U.S. provisional patent application Ser. No. 63/193,777 filed May 27, 2021, by inventors Thomas Deeds et al. and entitled SYSTEM FOR ASSOCIATING MEDICAL DEVICE DATA; U.S. provisional patent application Ser. No. 63/245,245 filed Sep. 17, 2021, by inventors Kirby Neihouser et al. and entitled SYSTEM FOR LOCATING PATIENT SUPPORT APPARATUSES; U.S. provisional patent application Ser. No. 63/245,279 filed Sep. 17, 2021, by inventors Jerald Trepanier et al. and entitled PATIENT SUPPORT APPARATUSES WITH PATIENT MONITORING; U.S. provisional patent application Ser. No. 63/245,289 filed Sep. 17, 2021, by inventors Madhu Thota et al. and entitled PATIENT SUPPORT APPARATUS COMMUNICATION AND LOCATION SYSTEM; and U.S. provisional patent application Ser. No. 63/306,279 filed Feb. 3, 2022, by inventors Madhu Thota et al. and entitled COMMUNICATION SYSTEM FOR PATIENT SUPPORT APPARATUSES, the complete disclosures of all of which are incorporated herein by reference.

BACKGROUND

The present disclosure relates to patient support apparatuses, such as beds, cots, stretchers, recliners, or the like. More specifically, the present disclosure relates to an exercise device adapted to be used by a patient while positioned on the patient support apparatus.

Medical devices, such as, but not limited to, exercise devices, are often used with a patient while the patient is positioned on a patient support apparatus. Such medical devices typically generate data regarding the patient that may be desirably forwarded to an electronic medical records server. In order for that data to be assigned to the medical records of the correct patient, one or more manual steps are typically required by a caregiver to associate the data from a particular medical device with a particular patient. In some cases, patient identity information is input into the medical device itself, and this identity information is transmitted with other data from the device to the EMR. This method requires that the transmitted patient data be properly secured against unauthorized disclosure so that unauthorized individuals do not gain access to the patient identify and his or her data. In other cases, an authorized individual may have to take manual steps to pair a radio onboard the medical device with a specific radio that is spaced away from the medical device.

SUMMARY

According to various embodiments, the present disclosure is directed to a system that overcomes past issues with associating data from medical devices, such as, but not limited to, exercise device with the correct patient and/or with a correct proxy for the patient (e.g. the patient support apparatus to which the patient is assigned, the room and/or room bay to which the patient is assigned, etc.). That is, the present disclosure provides a system and method for automatically associating a medical device, such as an exercise device, with the patient (or a proxy for the patient) if the medical device is positioned within a predetermined volume of space that surrounds all, or a portion of, the patient support apparatus. The automatic association allows data generated from the medical device to be properly categorized and, in some cases, stored in the correct electronic medical record for a particular patient. In the specific case of an exercise device, data such as the number of reps, exercise start and stop times, duration of exercise time, calories burnt, etc. may be automatically sent to a healthcare facility server with association data that enables the data to be automatically associated with the correct patient, thereby avoiding the need for an authorized user to manually associate the exercise device with a specific patient.

According to a first aspect of the present disclosure, an exercise device is provided for a patient to use while the patient is positioned on a patient support apparatus. The exercise device includes a first connector, a patient-contacting portion, a first elastic portion, a sensor, and a wireless transceiver. The first connector is adapted to be releasably coupled to a first location of the patient support apparatus. The patient-contacting portion is adapted to contact a portion of the patient's body. The first elastic portion is positioned between the first connector and the patient-contacting portion, and it is adapted to allow the patient to move the patient-contacting portion from a retracted position to an extended position. The sensor is adapted to automatically detect movement of the patient-contacting portion between the retracted and extended positions. The wireless transceiver is adapted to transmit movement data derived from the sensor to a recipient device.

According to other aspects of the present disclosure, the movement data may include a rep count corresponding to the number of times the patient moves the patient-contacting portion from the retracted position to the extended position.

In some embodiments, the wireless transceiver is a Bluetooth transceiver.

In some embodiments, the exercise device further includes a second connector adapted to be releasably coupled to a second location of the patient support apparatus, and a second elastic portion positioned between the second connector and the patient-contacting portion. In such embodiments, the second elastic portion is also adapted to allow the patient to move the patient-contacting portion from the retracted position to the extended position.

In some embodiments, the first and second connectors are adapted to releasably attach to first and second siderails of the patient support apparatus.

The patient-contacting portion, in some embodiments, is a foot pad and the exercise device is adapted to allow the patient to perform leg extensions. In such embodiments, the first and second elastic portions are adapted to provide resistance to the patient's legs moving the foot pad from the retracted position to the extended position.

In some embodiments, the sensor includes one or more accelerometers adapted to detect acceleration of the foot pad as it moves between the extended and retracted positions.

In some embodiments, the exercise device further includes a first location transceiver adapted to communicate with a second location transceiver physically separated from the exercise device. The first location transceiver is adapted to determine position information regarding a relative position of the first location transceiver to the second location transceiver. In some such embodiments, the recipient device is a second wireless transceiver positioned onboard the patient support apparatus.

In some embodiments, the wireless transceiver and second wireless transceiver are Bluetooth transceivers.

The first location transceiver, in some embodiments, is an ultra-wideband transceiver adapted to communicate with the second location transceiver via ultra-wideband signals.

The sensor, in some embodiments, includes a gyroscope.

The recipient device, in some embodiments, is one of a smart phone, tablet computer, or portable computer.

An exercise system according to another embodiment of the present disclosure includes a patient support apparatus and an exercise device. The exercise device includes a first connector adapted to be releasably coupled to a first location of the patient support apparatus; a patient-contacting portion adapted to contact a portion of the patient's body and to be resistively moved between a first position and a second position; a first location transceiver; and a sensor adapted to automatically detect movement of the patient-contacting portion between the first and second positions. The patient support apparatus includes a support surface adapted to support a person; a second location transceiver adapted to wirelessly communicate with the first location transceiver positioned on the exercise device; and a controller. The second location transceiver is adapted to generate a first location estimate of the first location transceiver, and the controller is adapted to use the first location estimate to determine if the exercise device is currently coupled to the patient support apparatus or not.

According to other aspects of the disclosure, the controller may be further adapted to associate the exercise device with the patient support apparatus if the controller determines the exercise device is coupled to the patient support apparatus.

In some embodiments, the controller determines that the exercise device is currently coupled to the patient support apparatus if it is positioned within a volume of space that partially, or wholly, encompasses the patient support apparatus.

The controller, in some embodiments, is further adapted to transmit a message to a remote server indicating that the exercise device is currently coupled to the patient support apparatus.

The patient support apparatus, in some embodiments, is further adapted to wirelessly receive movement data from the exercise device, wherein the movement data is derived from the sensor.

In some embodiments, the controller is further adapted to forward the movement data to a remote server. The controller may additionally be adapted to forward a first unique identifier corresponding to the patient support apparatus and a second unique identifier associated with a current location of the patient support apparatus to the remote server.

In some embodiments, the movement data includes a rep count corresponding to a number of times the patient moves the patient-contacting portion between the first and second positions.

The exercise device, in some embodiments, further includes a first elastic portion positioned between the first connector and the patient-contacting portion; a second connector adapted to be releasably coupled to a second location of the patient support apparatus; and a second elastic portion positioned between the second connector and the patient-contacting portion. In such embodiments, the first and second elastic portions are adapted to resist movement of the patient-contacting portion from the first position to the second position.

In some embodiments, the patient-contacting portion is a foot pad and the exercise device is adapted to allow the patient to perform leg extensions while seated on the patient support apparatus.

The system, in some embodiments, further includes a stationary unit mounted to a fixed location of a healthcare facility. The stationary unit includes a third location transceiver adapted to wirelessly communicate with the first location transceiver positioned on the exercise device. The third location transceiver is adapted to generate a second location estimate of the first location transceiver and to forward the second location estimate to the controller. The controller is further adapted to use the second location estimate to determine if the exercise device is currently coupled to the patient support apparatus or not.

The patient support apparatus, in some embodiments, further includes a third location transceiver adapted to wirelessly communicate with the first location transceiver positioned on the exercise device. The third location transceiver is adapted to generate a second location estimate of the first location transceiver and to forward the second location estimate to the controller. The controller is further adapted to use the second location estimate to determine if the exercise device is currently coupled to the patient support apparatus or not.

In some embodiments, the exercise device further includes a wireless transceiver adapted to transmit movement data derived from the sensor to a recipient device. The recipient device, in some embodiments, may be one of a smart phone, tablet computer, a portable computer, or the patient support apparatus.

In some embodiments, the wireless transceiver is a Bluetooth transceiver.

In some embodiments, the first location transceiver is an ultra-wideband transceiver adapted to communicate with the second location transceiver via ultra-wideband signals.

The sensor, in some embodiments, includes one or more accelerometers adapted to detect acceleration of the patient-contacting portion as it moves between the first and second positions.

An exercise system according to another embodiment of the present disclosure includes a patient support apparatus and an exercise device. The exercise device includes the following: (i) a patient-contacting portion adapted to contact a portion of the patient's body, the patient-contacting portion adapted to be resistively moved between a first position and a second position; (ii) a first location transceiver; (iii) a first wireless communication transceiver; and (iv) a sensor adapted to automatically detect movement of the patient-contacting portion between the first and second positions. The patient support apparatus includes the following: (a) a support surface adapted to support a person; (b) a second location transceiver adapted to wirelessly communicate with the first location transceiver positioned on the exercise device; (c) a second wireless communication transceiver; and (d) a controller adapted to automatically pair the second wireless communication transceiver with the first wireless communication transceiver based on location information derived from communications between the first and second location transceivers. The automatic pairing takes place without requiring any manual instruction from a user regarding the first wireless communication transceiver.

In some embodiments, the first wireless communication transceiver is further adapted to wirelessly receive movement data from the exercise device, wherein the movement data is derived from the sensor.

The patient support apparatus, in some embodiments, includes a network transceiver adapted to communicate with a local area network of a healthcare facility. In such embodiments, the controller may further be adapted to forward the movement data to a remote server via the network transceiver.

The controller, in some embodiments, is further adapted to forward a first unique identifier corresponding to the patient support apparatus and a second unique identifier associated with a current location of the patient support apparatus to the remote server.

In some embodiments, the movement data includes a rep count corresponding to a number of times the patient moves the patient-contacting portion between the first and second positions.

The exercise device, in some embodiments, further includes a first connector adapted to be releasably coupled to a first location of the patient support apparatus; a first elastic portion positioned between the first connector and the patient-contacting portion; a second connector adapted to be releasably coupled to a second location of the patient support apparatus; and a second elastic portion positioned between the second connector and the patient-contacting portion. In such embodiments, the first and second elastic portions are adapted to resist movement of the patient-contacting portion from the first position to the second position. Further, in some such embodiments, the patient-contacting portion is a foot pad and the exercise device is adapted to allow the patient to perform leg extensions while seated on the patient support apparatus.

The exercise system, in some embodiments, further includes a stationary unit mounted to a fixed location of a healthcare facility. The stationary unit includes a third location transceiver adapted to wirelessly communicate with the first location transceiver positioned on the exercise device. In such embodiments, the controller is further adapted to use information derived from communications between the third location transceiver and the first location transceiver to automatically pair the second wireless communication transceiver with the first wireless communication transceiver.

The patient support apparatus, in some embodiments, further includes a third location transceiver adapted to wirelessly communicate with the first location transceiver positioned on the exercise device. In such embodiments, the controller is further adapted to use information derived from communications between the third location transceiver and the first location transceiver to automatically pair the second wireless communication transceiver with the first wireless communication transceiver.

In some embodiments, the first and second wireless communication transceivers are both Bluetooth transceivers.

In some embodiments, the first location transceiver is an ultra-wideband transceiver adapted to communicate with the second location transceiver via ultra-wideband signals.

The sensor, in some embodiments, includes one or more accelerometers adapted to detect acceleration of the patient-contacting portion as it moves between the first and second positions.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
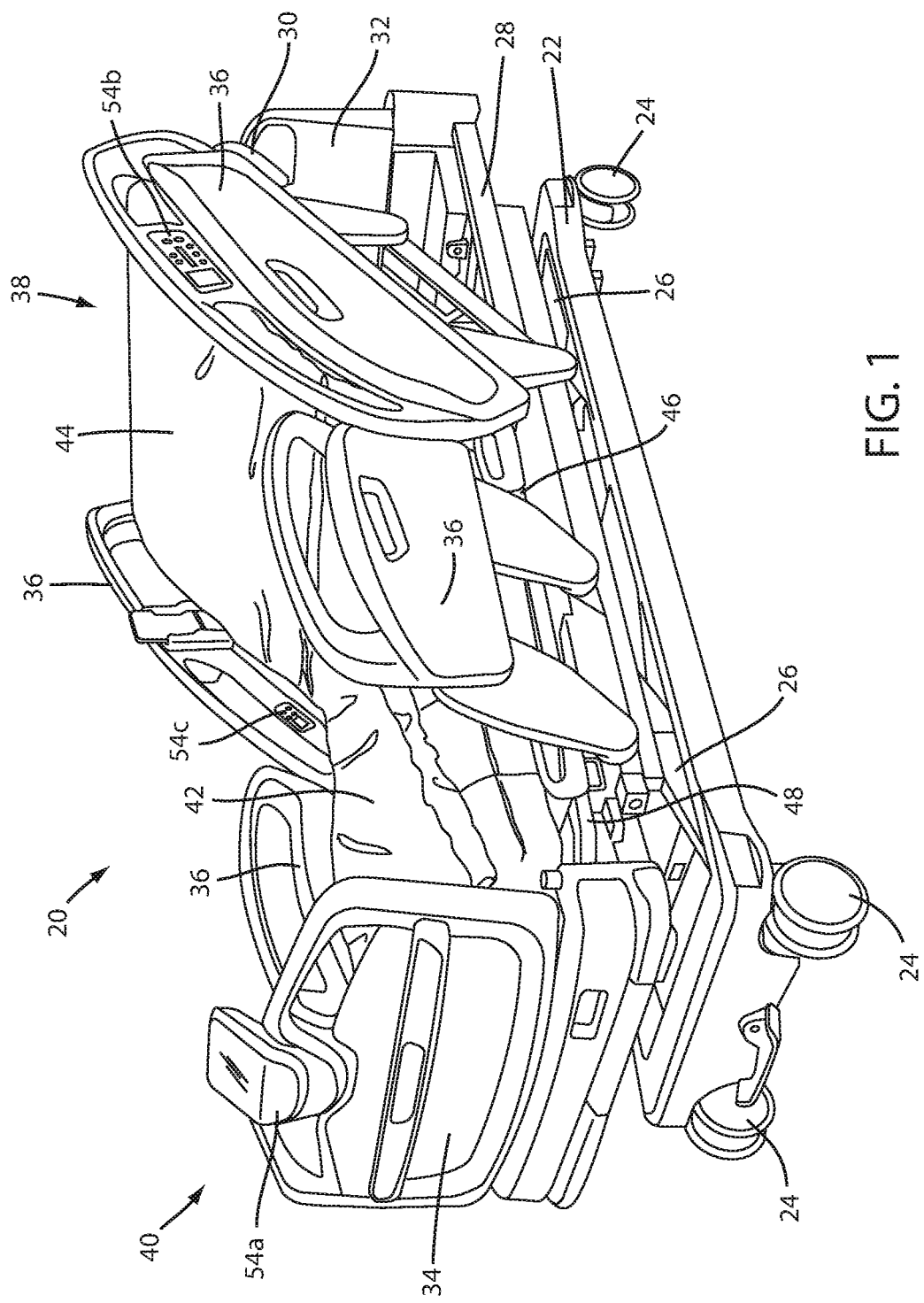
FIG. 1 is a perspective view of a patient support apparatus according to a first embodiment of the present disclosure.

An illustrative patient support apparatus 20 according to an embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. The top surface of the mattress 42 or other cushion forms a support surface for the occupant. In some embodiments, the mattress 42 includes one or more inflatable bladders that are controllable via a blower, or other source of pressurized air. In at least one embodiment, the inflation of the bladders of the mattress 42 is controllable via electronics and built into patient support apparatus 20. In one such embodiments, mattress 42 may take on any of the functions and/or structures of any of the mattresses disclosed in commonly assigned U.S. Pat. No. 9,468,307 issued Oct. 18, 2016, to inventors Patrick Lafleche et al., the complete disclosure of which is incorporated herein by reference. Still other types of mattresses may be used.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the construction of patient support apparatus 20 may include the same, or nearly the same, structures as the Model 3002 S3 bed manufactured and sold by Stryker Corporation of Kalamazoo, Mich. This construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. In still another embodiment, the construction of patient support apparatus 20 may include the same, or nearly the same, structure as the Model 3009 Procuity MedSurg bed manufactured and sold by Stryker Corporation of Kalamazoo, Mich. This construction is described in greater detail in the Stryker Maintenance Manual for the 3009 Procuity MedSurg bed (publication 3009-009-002, Rev. A.0), published in 2020 by Stryker Corporation of Kalamazoo, Mich.

It will be understood by those skilled in the art that patient support apparatus 20 can be designed with still other types of constructions, such as, but not limited to, those described in commonly assigned, U.S. Pat. No. 7,690,059 issued Apr. 6, 2010, to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The overall construction of patient support apparatus 20 may also take on still other forms different from what is disclosed in the aforementioned references provided the patient support apparatus includes the functions and features discussed in greater detail below.

Figure 2:
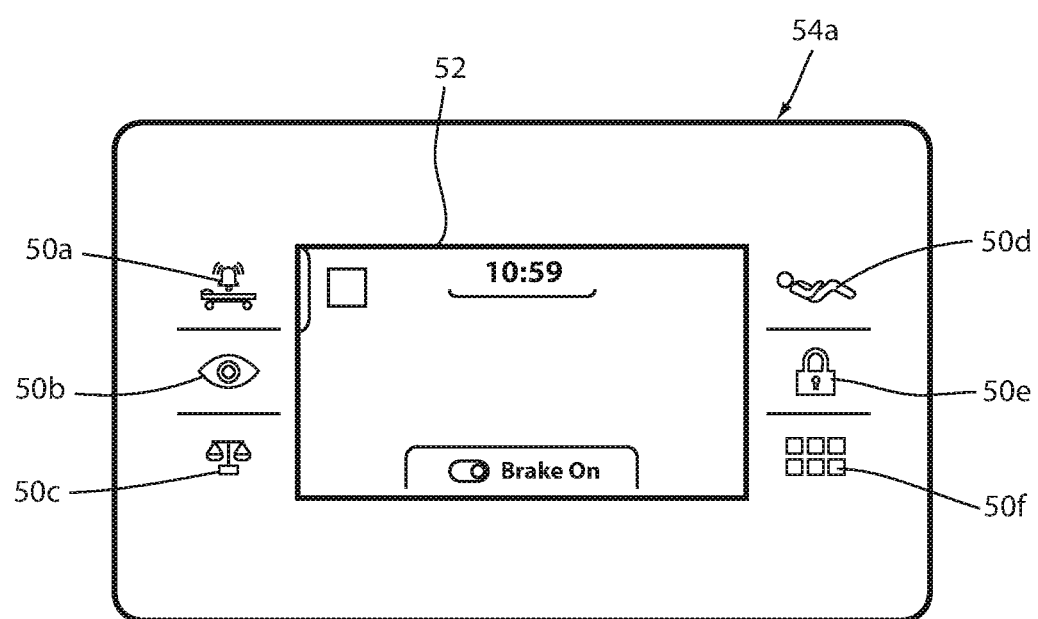
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54a, a pair of outer siderail control panels 54b (only one of which is visible), and a pair of inner siderail control panels 54c (only one of which is visible). Footboard control panel 54a and outer siderail control panels 54b are intended to be used by caregivers, or other authorized personnel, while inner siderail control panels 54c are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54a allow a user to control one or more of the following: change a height of support deck 30, raise or lower head section 44, activate and deactivate a brake for wheels 24, arm and disarm an exit detection system 56 (FIG. 5) and, as will be explained in greater detail below, communicate with the particular IT infrastructure installed in the healthcare facility in which patient support apparatus 20 is positioned. One or both of the inner siderail control panels 54c also include at least one control that enables a patient to call a remotely located nurse (or other caregiver). In addition to the nurse call control, one or both of the inner siderail control panels 54c also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54c include, but are not limited to, the volume, the channel, the closed-captioning, and/or the power state of the television. With respect to the room and/or night lights, the features that may be controlled by one or more controls 50 on control panel 54c include the on/off state and/or the brightness level of these lights.

Figure 5:
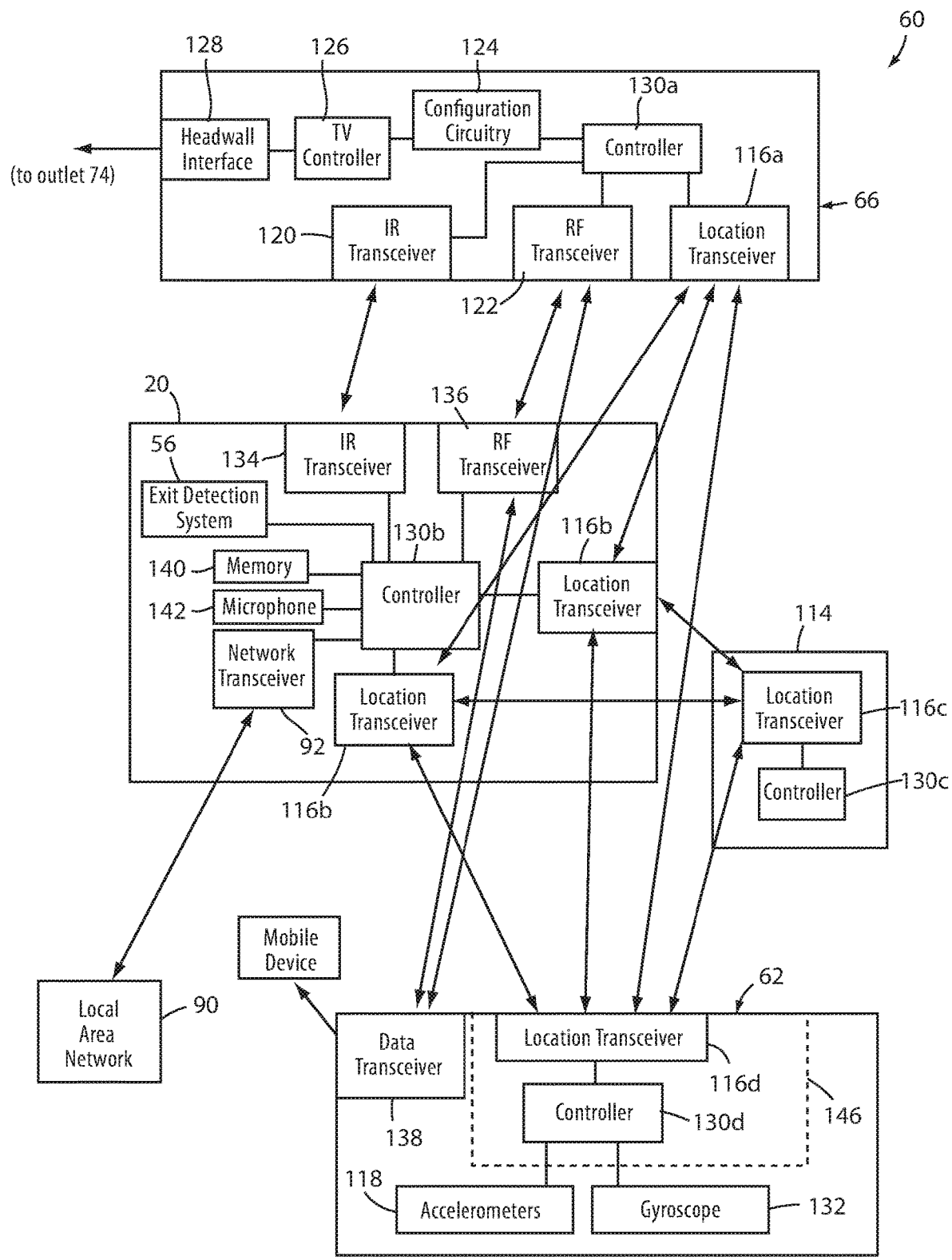
FIG. 5 is a block diagram of several components of the system of FIG. 4.

Control panel 54a includes a display 52 (FIG. 2) configured to display a plurality of different screens thereon. Surrounding display 52 are a plurality of navigation controls 50a-f that, when activated, cause the display 52 to display different screens on display 52. More specifically, when a user presses navigation control 50a, control panel 54a displays an exit detection control screen on display 52 that includes one or more icons that, when touched, control an onboard exit detection system 56 (FIG. 5). The exit detection system 56 is as adapted to issue an alert when a patient exit from patient support apparatus 20. Exit detection system 56 may include any of the features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Other types of exit detection systems may be included within patient support apparatus 20.

When a user pressed navigation control 50b (FIG. 2), control panel 54 displays a monitoring control screen that includes a plurality of control icons that, when touched, control an onboard monitoring system built into patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems may be included within patient support apparatus 20.

When a user presses navigation control 50c, control panel 54a displays a scale control screen that includes a plurality of control icons that, when touched, control the scale system of patient support apparatus 20. Such a scale system may include any of the features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. The scale system may utilize the same force sensors that are utilized by the exit detection system 56, or it may utilize one or more different sensors. Other scale systems besides those mentioned above in the '254 and '954 applications may alternatively be included within patient support apparatus 20.

When a user presses navigation control 50d, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50d may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of motion control screens may be included on patient support apparatus 20.

When a user presses navigation control 50e, control panel 54a displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosure of which is incorporated herein by reference. Other types of motion lockouts may be included within patient support apparatus 20.

When a user presses on navigation control 50f, control panel 54a displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of menus and/or settings may be included within patient support apparatus 20. In at least one embodiment, utilization of navigation control 50f allows a user to navigate to a screen that enables a user to configure the communication settings between patient support apparatus 20 and a headwall unit 66 (see, e.g. FIGS. 4-5). Examples of the type of communication settings that may be configured in this manner are disclosed in, and illustrated in FIGS. 9-15 of, commonly assigned U.S. patent application Ser. No. 63/26,937 filed May 19, 2020, by inventors Alexander Bodurka et al. and entitled PATIENT SUPPORT APPARATUSES WITH HEADWALL COMMUNICATION, the complete disclosure of which is incorporated herein by reference.

For all of the navigation controls 50a-f (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50a-f. It will also be understood that, although navigation controls 50a-f have all been illustrated in the accompanying drawings as dedicated controls that are positioned adjacent display 52, any one or more of these controls 50a-f could alternatively be touchscreen controls that are displayed at one or more locations on display 52. Still further, although controls 50a-f have been shown herein as buttons, it will be understood that any of controls 50a-f could also, or alternatively, be switches, dials, or other types of non-button controls.

Figure 3:
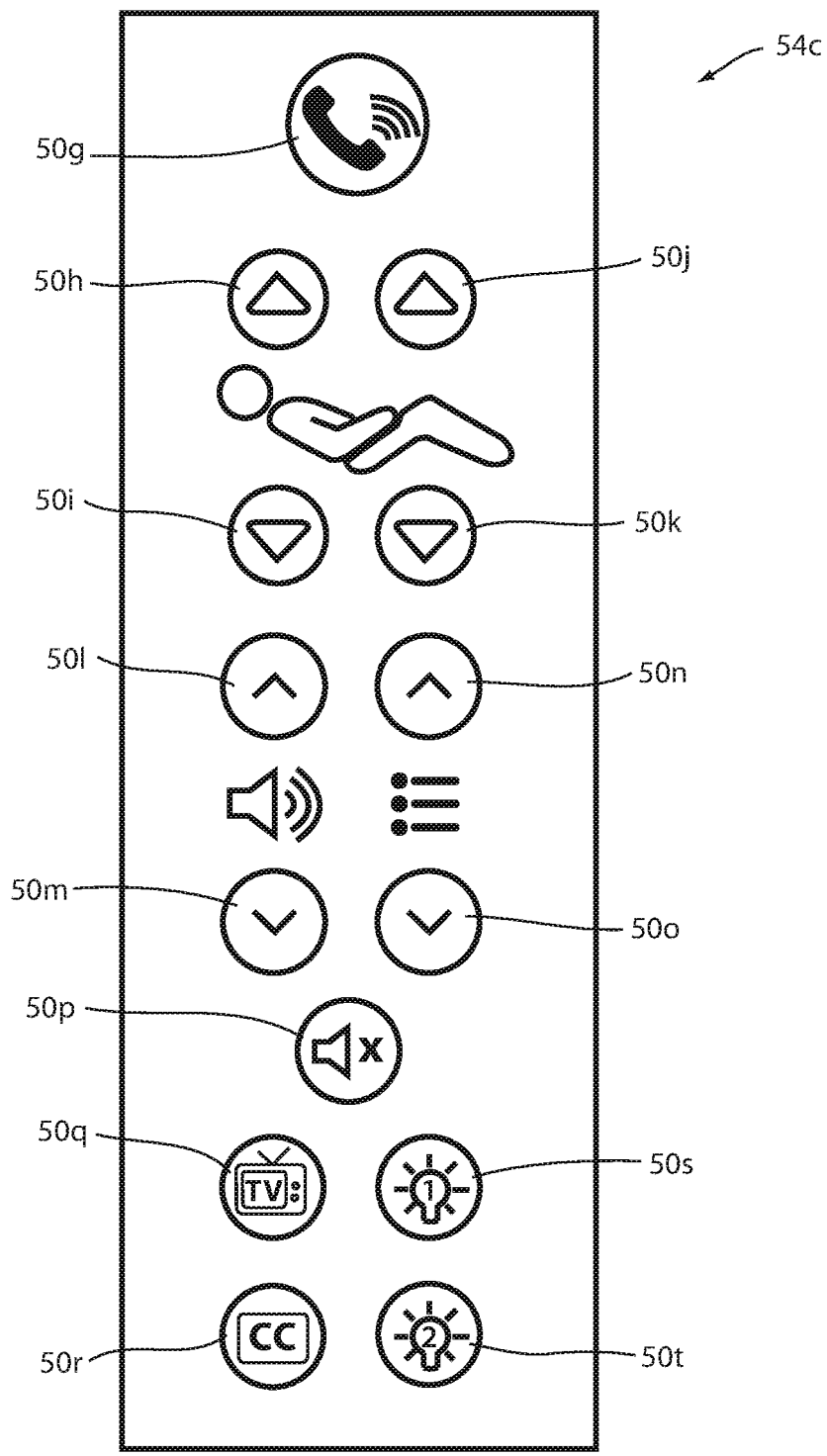
FIG. 3 is a plan view of an illustrative patient control panel of the patient support apparatus of FIG. 1.

FIG. 3 illustrates one example of a patient control panel 54c that may be incorporated into patient support apparatus 20 and positioned at a location on patient support apparatus 20 that is convenient for a patient to access while supported on support deck 30, such as on an interior side of one of the siderails 36. Control panel 54c includes a plurality of controls 50g-t that are intended to be operated by a patient. A nurse call control 50g, when pressed by the patient, sends a signal to a nurse call system requesting that a remotely positioned nurse talk to the patient. A Fowler-up control 50h, when pressed by the patient, causes a motorized actuator onboard patient support apparatus 20 to raise Fowler section 44 upwardly. A Fowler-down control 50i, when pressed by the patient, causes the motorized actuator to lower Fowler section 44 downwardly. A gatch-up control 50j, when pressed by the patient, causes another motorized actuator to raise a knee section of support deck 30, while a gatch-down control 50k causes the motorized actuator to lower the knee section of support deck 30.

A volume-up control 50l, when pressed by the patient, causes patient support apparatus 20 to send a signal to an in-room television instructing it to increase its volume, while a volume down control 50m, when pressed, causes patient support apparatus 20 to send a signal to the television instructing it to decrease its volume. A channel-up control 50n, when pressed by the patient, causes patient support apparatus 20 to send a signal to the television instructing it to increase the channel number, while a channel-down control 50o, when pressed, causes patient support apparatus 20 to send a signal to the television instructing it to decrease the channel number.

A mute control 50p, when pressed, causes patient support apparatus 20 to send a signal to the television instructing it to either mute itself or unmute itself, depending upon whether the television is currently muted or unmuted. In other words, mute control 50p is a toggle control that alternatingly sends mute and unmute commands to the television when it is pressed.

Power control 50q is a toggle control that, when pressed, sends a signal to the television to either turn on or turn off, depending upon the television's current power status. Closed-captioning control 50r is another toggle control that, when pressed, sends a signal to the television to either turn on its closed-captioning feature or to turn off its closed captioning feature, depending upon whether the closed-captioning feature is currently on or off.

Control 50s is a toggle control that, when pressed, sends a signal to a first light to either turn on or turn off, depending upon the current state of that first light. Control 50t is another toggle control that, when pressed, sends a signal to a second light to either turn on or turn off, depending upon the current state of that second light. In some embodiments, the first light is a reading light and the second light is a room light, both of which are positioned off-board the patient support apparatus 20.

It will be understood that not only the number of controls 50 on control panel 54c, but also the functions of the controls 50 on control panel 54c, the layout of the controls 50 on control panel 54c, and/or other aspects of control panel 54c may be modified from what is shown in FIG. 3. In some embodiments, control panel 54c is implemented on a pendant controller that includes a cable that is plugged into a port on patient support apparatus 20. In other embodiments, one or more of the controls 50 of control panel 54c may be omitted, augmented, and/or split amongst other controls panels and/or locations. Still other manners of implementing control panel 54c are also possible.

Figure 4:
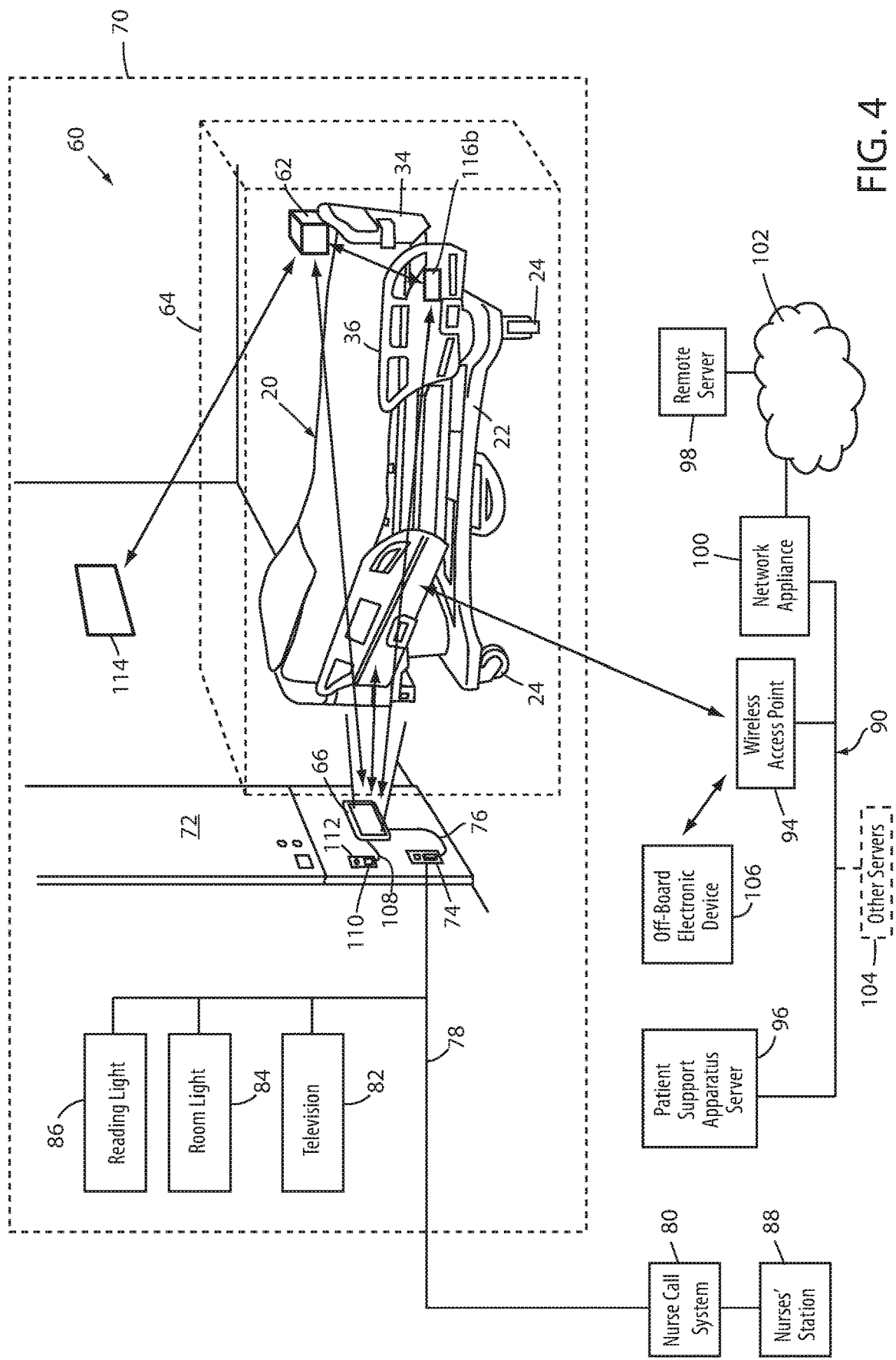
FIG. 4 is a diagram of a first embodiment of a system for automatically detecting the position of tagged medical devices positioned in a room of a healthcare facility.

FIG. 4 illustrates a system 60 for determining the location of one or more tagged medical devices 62 relative to patient support apparatus 20 and/or a volume of space 64 defined within a room 70 of a conventional healthcare facility, such as, but not limited to, a hospital. Such tagged medical devices 62 include, but are not limited to, exercise devices (discussed in greater detail below), heel care boots, IV stands and/or poles, ventilators, patient monitors, vital sign detectors, and/or any other types of devices that are used in the treatment, monitoring, and/or rehabilitation of the patient.

System 60 includes patient support apparatus 20, one or more headwall units 66, and one or more location transceivers 116. One or more of the location transceivers 116 may be positioned at known and fixed locations within the healthcare facility, and one or more of the location transceivers 116 may also or alternatively be coupled to patient support apparatus 20. When coupled to patient support apparatus 20, location transceivers 116 are positioned therein at known locations on the body of patient support apparatus 20. As will be discussed in greater detail below, location transceivers 116 are adapted to determine if a tagged medical device 62 is positioned within the volume of space 64. If so, system 60 treats the tagged medical device 62 in a first manner, and if not, system 60 treats the tagged medical device 62 in a second and different manner, as will be discussed in greater detail below. In general, if the tagged medical device is positioned inside the space volume 64, system 60 concludes that the device 62 is associated with the patient assigned to the particular patient support apparatus 20 that is also positioned within the same volume of space 64 (either wholly or partially).

As shown in FIG. 4, room 70 includes a headwall 72 into which a conventional communications outlet 74 is physically integrated. Communications outlet 74 is adapted to receive a nurse call cable 76 that physically connects at its other end either to patient support apparatus 20 (not shown) or to a wireless headwall unit 66 (shown in FIG. 4). In many healthcare facilities, communication outlet 74 includes a 37-pin connector, although other types of connectors are often found in certain healthcare facilities. As will be discussed in greater detail below, headwall unit 66 and nurse call cable 76 allow patient support apparatus 20 to communicate with a nurse call system, and one or more room devices positioned within room 70.

Communication outlet 74 is electrically coupled to one or more cables, wires, or other conductors 78 that electrically couple the communication outlet 74 to a nurse call system 80 and one or more room devices, such as a television 82, a room light 84, and/or a reading light 86. Conductors 78 are typically located behind headwall 72 and not visible. In some healthcare facilities, conductors 78 may first couple to a room interface circuit board that includes one or more conductors 78 for electrically coupling the room interface circuit board to room devices 82, 84, 86 and/or nurse call system 80. Still other communicative arrangements for coupling communication outlet 74 to nurse call system 80 and/or one or more room devices 82, 84, 86 are possible.

Room devices 82, 84, 86 are conventional room devices that are typically present in a conventional hospital room. In most cases, the particular brand and model of the television 82 and/or lights 84, 86 will vary from healthcare facility to healthcare facility, and may vary from room to room within the same healthcare facility. The different models and/or brands of televisions 82, room lights 84, and/or reading lights 86 are often controlled in different manners. For example, the signals that are input into a first brand of television in order to change a channel may require a first voltage level, while the signals that are input into a second brand of television in order to change the channel may require a second voltage level. Still further, apart from differences in voltage levels, the sequence of bits and/or other information that is sent to a television to change the channel, for example, may vary from brand to brand, or from model to model. Still other aspects of the control of the television 82 and/or lights 84, 86 may vary from brand to brand and/or from model to model. Thus, in order for a patient to properly control the television 82 and/or lights 84, 86 using one of the patient control panels 54c, patient support apparatus 20 or headwall unit 66 need to be properly configured to match the particular television 82 and/or lights 84, 86 that are positioned in the same room as the patient support apparatus 20. In the systems described herein, headwall units 66 are configured to match the associated televisions 82 and/or lights 84, 86, as well as the associated nurse call system 80.

Returning to FIG. 4, nurse call cable 76 enables patient support apparatus 20 to communicate with nurse call system 80 and/or room devices 82, 84, 86. A patient supported on patient support apparatus 20 who activates a nurse call control (e.g. 50g; see FIG. 3) on patient support apparatus 20 causes a signal to be wirelessly sent from patient support apparatus 20 to headwall unit 66, which in turn conveys the signal via nurse call cable 76 to the nurse call system 80, which forwards the signal to a one or more remotely located nurses (e.g. nurses at one or more nurses' stations 88). If the patient activates one or more room device controls (e.g. controls 50l-t; see FIG. 3), one or more wireless signals are conveyed to headwall unit 66, which in turn sends appropriate signals via nurse call cable 76 to communication outlet 74 and the room devices 82, 84, 86 that change one or more features of these devices (e.g. the volume, channel, on/off state, etc.).

As is also shown in FIG. 4, patient support apparatus 20 is further configured to communicate with a local area network 90 of the healthcare facility. In the embodiment shown in FIG. 4, patient support apparatus 20 includes a wireless network transceiver 92 (FIG. 5) that communicates wirelessly with local area network 90. Network transceiver 92 is, in at least some embodiments, a WiFi transceiver (e.g. IEEE 802.11) that wirelessly communicates with one or more conventional wireless access points 94 of local area network 90. In other embodiments, network transceiver 92 may be a wireless transceiver that uses conventional 5G technology to communicate with LAN 90, a server hosted thereon, and/or another device. In some embodiments, network transceiver 92 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

In some embodiments, network transceiver 92 is a wired transceiver that is adapted to allow patient support apparatus 20 to communicate with network 90 via a wired connection, such as an Ethernet cable that plugs into an Ethernet port (e.g. an RJ-45 style port, an 8P8C port, etc.) built into patient support apparatus 20. In still other embodiments, patient support apparatus 20 includes both a wired transceiver 92 for communicating with network 90 via a wired connection and a wireless transceiver 92 for wirelessly communicating with network 90.

Patient support apparatus 20 is configured to communicate with one or more servers on local area network 90 of the healthcare facility. One such server is a patient support apparatus server 96. Patient support apparatus server 96 is adapted, in at least one embodiment, to receive status information from patient support apparatuses 20 positioned within the healthcare facility and distribute this status information to caregivers, other servers, and/or other software applications. In some embodiments, patient support apparatus server 96 is configured to communicate at least some of the status data received from patient support apparatuses 20 to a remote server 98 that is positioned geographically remotely from the healthcare facility. Such communication may take place via a network appliance 100, such as, but not limited to, a router and/or a gateway, that is coupled to the Internet 102. The remote server 98, in turn, is also coupled to the Internet 102, and patient support apparatus server 96 is provided with the URL and/or other information necessary to communicate with remote server 98 via the Internet connection between network 90 and server 98.

In some alternative embodiments, patient support apparatus 20 may be configured to communicate directly with one or more cloud-based servers, such as remote server 98, without utilizing patient support apparatus server 96. That is, in some embodiments, patient support apparatuses 20 may be configured to communicate directly with a remote server without relying upon any locally hosted servers (e.g. servers hosted on LAN 90). In one such embodiment, patient support apparatus 20 utilizes Microsoft's Azure could computing service to directly connect to one or more remote servers 98 without utilizing server 96. In some such embodiments, network appliance 100 is a router configured to support such direct connections. Still other types of direct-to-cloud connections may be utilized with one or more of patient support apparatuses 20.

As will be discussed in greater detail below, patient support apparatus server 96 may also carry out additional functions, such as, but not limited to, determining the location of one or more tagged medical devices 62 positioned within room 70. Depending upon whether the location of the medical device 62 is within a volume of space 64 defined within the room, and/or within a threshold distance of patient support apparatus 20, patient support apparatus server 96 may be configured to determine whether to allow the medical device 62 to join a wireless network that is associated with the patient assigned to patient support apparatus 20; to automatically associate the tagged medical device 62 (and/or its data) with a particular patient, patient support apparatus, room, and/or bay identifier; to automatically forward data to server 96; and/or to take other actions. In other embodiments, one or more of these functions may be carried out by one or more controllers onboard patient support apparatus 20 or headwall unit 66, and/or a combination of these devices, either alone or in conjunction with server 96 (and/or server 98).

It will be understood that the architecture and content of local area network 90 will vary from healthcare facility to healthcare facility, and that the example shown in FIG. 4 is merely one example of the type of network a healthcare facility may be employ. Typically, additional servers 104 will be hosted on network 90 and one or more of them may be adapted to communicate with patient support apparatus server 96. For example, an electronic health record server will typically be present in any healthcare facility, and in some embodiments discussed herein, it will be in communication with patient support apparatus server 96 in order to receive patient data that is to be recorded in a patient's health record (e.g. weight readings taken from the scales built into patient support apparatuses 20; therapies provided to patients using a powered mattress 42 onboard patient support apparatuses 20, data from a medical device 62 that is determined to be associated with the patient assigned to patient support apparatus 20, etc.). Local area network 90 will also typically allow one or more electronic devices 106 to access the local area network 90 via wireless access points 106. Such electronic devices 106 include, but are not limited to, smart phones, tablet computers, portable laptops, desktop computers, and other types of electronic devices that include a WiFi capability and that are provided with the proper credentials (e.g. SSID, password, etc.) to access network 90 (and, in at least some situations, patient support apparatus server 96).

Headwall units 66 are adapted to wirelessly receive signals from patient support apparatus 20 and deliver the signals to communications outlet 74 in a manner that matches the way the signals would otherwise be delivered to communications outlet 74 if a conventional nurse call cable 76 were connected directly between patient support apparatus 20 and communications outlet 74. In other words, patient support apparatus 20 and headwall unit 66 cooperate to provide signals to communications outlet 74 in a manner that is transparent to communications outlet 74 such that outlet 74 cannot detect whether it is in communication with patient support apparatus 20 via a wired connection or it is in communication with patient support apparatus 20 via a wireless connection between patient support apparatus 20 and headwall unit 66 (the latter of which is in wired communication with outlet 74). In this manner, a healthcare facility can utilize the wireless communication abilities of one or more patient support apparatuses 20 without having to make any changes to their existing communication outlets 74.

In addition to sending signals received from patient support apparatus 20 to communications outlet 74, headwall units 66 are also adapted to forward signals received from communications outlet 74 to patient support apparatus 20. Headwall units 66 are therefore adapted to provide bidirectional communication between patient support apparatus 20 and communications outlet 74. Such communication includes, but is not limited to, communicating command signals from any of controls 50 and/or from any of electronic devices 106 to corresponding room devices 82, 84, and/or 86. Such communication also includes communicating audio signals between a person supported on patient support apparatus 20 and a caregiver positioned remotely from patient support apparatus 20. The audio signals received by headwall units 66 from a microphone on patient support apparatus 20 are forwarded to communications outlet 74, and the audio signals received from communications outlet 74 are forwarded to a speaker onboard patient support apparatus 20.

Nurse call cable 76, in some embodiments, includes a conventional 37 pin connector on each end, one of which is adapted to be inserted into outlet 74 and the other one of which is adapted to be inserted into headwall unit 66. Such 37 pin connections are one of the most common types of connectors found on existing headwalls of medical facilities for making connections to the nurse call system 80 and room devices 82, 84, and 86. Headwall unit 66 and nurse call cable 76 are therefore configured to mate with one of the most common type of communication outlets 74 used in medical facilities. Such 37 pin connectors, however, are not the only type of connectors, and it will be understood that headwall unit 66 can utilize different types of connectors that are adapted to electrically couple to different types of nurse call cables 76 and/or different types of communication outlets 74. One example of such an alternative communications outlet 74 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 74 and corresponding connectors may be utilized.

Headwall unit 66 (FIG. 4) also includes an electrical cord 108 having a plug 110 positioned at a far end that is adapted to be inserted into a conventional electrical outlet 112. Electrical cord 108 enables headwall unit 66 to receive power from the mains electrical supply via outlet 112. It will be appreciated that, in some embodiments, headwall unit 66 is battery operated and cord 108 may be omitted. In still other embodiments, headwall unit 66 may be both battery operated and include cord 108 so that in the event of a power failure, battery power supplies power to headwall unit 66, and/or in the event of a battery failure, electrical power is received through outlet 112.

In addition to any of the structures and functions described herein, headwall units 66 may be configured to communicate location data to patient support apparatus 20 that enables patient support apparatus 20 and/or patient support apparatus server 96 to determine the location of patient support apparatus 20 within the healthcare facility. Such location determination may be carried out in any of the manners disclosed in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

Headwall units 66 may also perform additional functions. In some embodiments, headwall units 66 may perform any of the functions performed by the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. In some embodiments, headwall units 66 may also, or alternatively, perform any of the same functions performed by the headwall interfaces 72 disclosed in commonly assigned U.S. patent application Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosure of which is also incorporated herein by reference. In still other embodiments, headwall units 66 may also, or alternatively, perform any of the same functions performed by the headwall units 66 disclosed in commonly assigned U.S. patent application Ser. No. 16/217,203 filed Dec. 12, 2018, by inventor Alexander Bodurka et al. and entitled SMART HOSPITAL HEADWALL SYSTEM, the complete disclosure of which is incorporated herein by reference.

In some embodiments, headwall units 66 may be constructed to include any or all of the functionality of the wireless headwall units disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference.

In some embodiments, headwall units 66 may also be constructed to include any or all of the functionality of the headwall units disclosed in commonly assigned U.S. patent application Ser. No. 63/26,937 filed May 19, 2020, by inventors Alexander Bodurka et al. and entitled PATIENT SUPPORT APPARATUSES WITH HEADWALL COMMUNICATION, the complete disclosure of which is also incorporated herein by reference.

Still further, in some embodiments, headwall units may be constructed to include any of the features and/or functions of the headwall units 144a disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference.

In some embodiments, patient support apparatus 20 and/or patient support apparatus server 96 may include any or all of the functionality of the patient support apparatuses and/or patient support apparatus servers described in any of the aforementioned commonly assigned U.S. patents and/or patent applications.

FIG. 5 depicts a block diagram of various components of one embodiment of system 60. These include patient support apparatus 20, headwall unit 66, a fixed medical device locator 114, and a tagged medical device 62. It will be understood that the components depicted in FIG. 5 are not necessarily a complete set of components, and that system 60 may additionally include one or more additional fixed medical device locators 114, one or more patient support apparatuses, and/or one or more additional headwall units 66. Further, it will be understood that the internal circuitry of each of these components may include more than what is shown in FIG. 5. For example, while headwall unit 66 is depicted in FIG. 5 to include only a single location transceiver 116a, it will be understood that it may include more than one of these. Similarly, although patient support apparatus 20 is depicted as including two location transceivers 116b, it may include more or less than these two. Still other variations of system 60 are possible, including, but not limited to, variations having fewer components than those shown in FIG. 5 (e.g. system 60, in some embodiments, may omit the fixed medical device locator 114) and variations have greater numbers of components.

As was noted, system 60 is adapted to determine if one or more medical devices 62 are positioned within a predefined volume of space 64 (FIG. 4). The predefined volume of space may be defined in a fixed manner relative to the dimensions of the room 70 (and thus stationary), or it may be defined relative to patient support apparatus 20 (and thus moveable as patient support apparatus 20 moves). When defined in fixed manner, volume 64 will typically include the space defined by a particular bay within the room 70. That is, it will encompass the volume typically occupied by the patient support apparatus 20 when the patient support apparatus 20 is in its customary position within a particular bay within the room 70. It will also typically encompass a relatively small amount of space surrounding the customary position of the patient support apparatus 20 (such as, but not limited to, about one to two feet beyond the perimeter of the patient support apparatus 20) in which medical devices 62 might be placed that are used with the patient on patient support apparatus 20 (e.g. an IV stand, an exercise device, a patient monitor, etc.). Although FIG. 4 depicts volume 64 as a generally rectangular volume, it will be understood that this is merely one example of the shape that volume 64 may take on. Other non-rectangular shapes and/or shapes having portions that are rectangular and portions that are non-rectangular, as well as still other shape combinations, may be used. Volume 64 generally corresponds to the volume of space in which a medical device 62 must be positioned in order for system 60 to associate it with that particular patient support apparatus 20 (and/or with the patient assigned to that patient support apparatus 20 and/or with the bay or room to which that patient is assigned).

In some embodiments, regardless of whether volume of space 64 is fixed or mobile, the size and/or shape of space volume 64 may be dynamic. That is, the size and/or shape of space 64 may vary in some embodiments. This size and/or shape variance may be based on one or more of the following factors: (a) the particular type, brand, model, or other characteristic of patient support apparatus 20; (b) the particular room, bay, or other environment in which patient support apparatus 20 is currently located; (c) the particular tagged medical device 62 whose location is being determined; and/or (d) the relatively proximity of another patient support apparatus 20. Thus, for example, system 60 is configured in some embodiments to assign larger space volumes 64 to certain models of patient support apparatus 20 that are larger than other models of patient support apparatuses 20. As another example, system 60, in some embodiments, alters the shape and/or enlarges the size of volume 64 in private hospital rooms when compared to the volume 64 that it utilizes in semi-private hospital rooms in which another patient support apparatus 20 is located. Still further, for example, system 60 may utilize larger space volumes 64 for medical devices 62 that are customarily positioned alongside patient support apparatus 20 rather than on patient support apparatus 20 (e.g. mobile IV stands that are supported on the floor versus heel care boots that are worn by the patient). As yet another example, system 60, in some embodiments, may reduce the size of, or otherwise change the shape of, volume 64 when a patient support apparatus 20 is positioned in relatively close proximity to another patient support apparatus 20 in order to avoid mistakenly assigning a tagged medical device 62 to the nearby, but incorrect, patient support apparatus 20. Still other examples of changing the size and/or shape of space volume 64 may be implemented.

Headwall unit 66 (FIG. 5), in some embodiments, includes an infrared transceiver 120, a Bluetooth transceiver 122, a headwall unit controller 130a, configuration circuitry 124, smart television control circuitry 126, and a headwall interface 128. Headwall unit 66 also includes at least one location transceiver 116a that, as will be described more below, is used in conjunction with other location transceivers 116b, 116c, etc. to determine the location of medical device 62. Infrared transceiver 120 is adapted to communicate with an infrared transceiver 134 of patient support apparatus 20 using infrared waves. Bluetooth transceiver 122 is adapted to communicate with Bluetooth transceiver 136 of patient support apparatus 20 using RF waves in accordance with the conventional Bluetooth standard (e.g. IEEE 802.14.1 and/or the standard maintained by the Bluetooth Special Interest Group (SIG) of Kirkland, Wash., USA. In some embodiments, transceivers 122 and 136 utilize Bluetooth Low Energy communications.

Headwall unit controller 130a is adapted to control the operation of transceivers 120, 122, configuration circuitry 124, TV controller 126, headwall interface 128, and location transceiver 116a. Headwall controller 130a and location transceiver 116a together define an "anchor point" that, as will be discussed further below, is adapted to determine the distance (as well as angular information, in some embodiments) between location transceiver 116a and the other location transceivers 116 of system 60. System 60 uses this distance and angular information to repetitively compute the location of tagged medical device 62 and to repetitively determine whether or not it is inside or outside of space volume 64. In some embodiments, location transceiver 116a, as well as the other location transceivers 116, are ultra-wideband transceivers. In other embodiments, location transceiver 116a, as well as the other location transceivers 116, are Bluetooth Low Energy transceivers. In still other embodiments, location transceiver 116a may be combined with RF transceiver 122 such that it is used both to communicate with patient support apparatus 20 and to determine a distance between itself and medical device 62. Location transceiver 116a, as with all of the location transceivers 116 discussed herein, may include an array of antennas that are used to assist in the determination of location. Different manners in which location transceivers 116 may determine the location of tagged medical device 62 are discussed in greater detail in commonly assigned U.S. patent application Ser. No. 63/132,514 filed Dec. 31, 2020, by inventors Alexander Bodurka et al. and entitled PATIENT SUPPORT APPARATUS AND MEDICAL DEVICE NETWORKS, the complete disclosure of which is incorporated herein by reference.

In some embodiments, one or more of the location transceivers 116 and their associated controllers are implemented as any of the Trimension™ ultra-wideband modules available from NXP Semiconductors of Austin, Tex. These modules include, but are not limited to, the Trimension™ UWB modules SR150, SR100T, SR040, NCJ29D5, and/or the OL23DO. Modules manufactured and/or marketed by other companies may also be used, including, but not limited to, the Decawave DWM1000, DWM3000, and/or DWM10001C modules (available from Decawave of Dublin, Ireland); the Nordic TSG5162 SiP module (available from Tsingoal Technology of Beijing, China); and/or the UWB hub, wand, and/or sensors available from Zebra technologies of Lincolnshire, Ill. Still other types of UWB and/or Bluetooth modules may be used to implement location transceivers 116.

Patient support apparatus 20 includes a controller 130b, a memory 140, the transceivers 134, 136 mentioned above, network transceiver 92, and, in some embodiments, one or more location transceivers 116b. As was noted previously, network transceiver 92 may be a WiFi transceiver, or other type of transceiver, that is adapted to communicate with local area network 90. Each location transceiver 116b of patient support apparatus 20 is positioned at a known location on patient support apparatus 20. This known location information may be stored in memory 140 and/or elsewhere, and may be defined with respect to any suitable common frame of reference. The known location information may include the spatial relationship between transceivers 116b and/or any other components of patient support apparatus 20. For example, in some embodiments, the known location information includes the spatial relationship not only between transceiver 116b themselves, but also the spatial relationships between transceivers 116b and the head end 38 (and/or IR transceiver 134) of patient support apparatus 20. This location information may be used to determine the orientation of patient support apparatus 20 with respect to headwall unit 66, headwall 72, a fixed locator 114, and/or another object or structure within the healthcare facility.

Controller 130b utilizes location transceivers 116b to determine distances between each transceiver 116b and medical device 62, as well as, distances between location transceivers 116b and any off-board location transceivers 116 that are part of system 60 (e.g. location transceivers 116a, 116c). The manners in which these distances may be determined may vary from embodiment to embodiment based upon which type of ultra-wideband or Bluetooth technology is used with location transceivers 116. In general, distances and/or angular information that is generated from the communications between location transceivers 116 may utilize Angle of Arrival (AoA) information, Time of Flight (TOF) information, Channel State Information, and/or other information to generate this information. In some embodiments, each location transceiver 116 includes an array of antennas that are used to generate this distance and/or angular information.

Patient support apparatus 20 also includes, in at least some embodiments, a microphone 142 that is used to detect the voice of the patient when the patient wants to speak to a remotely positioned nurse. The patient's voice is converted to audio signals by microphone 142 and controller 130b is adapted to forward these audio signals to communications outlet 74. When a cable 76 is coupled between patient support apparatus 20 and outlet 74, controller 130b forwards these audio signals to outlet 74 via the cable. When no such cable 76 extends between patient support apparatus 20 and outlet 74, controller 130b wirelessly forwards these audio signals to headwall unit 66 (using transceiver 122 and/or 120) and controller 130a of headwall unit 66 forwards these audio signals to outlet 74. As was noted, outlet 74 is in electrical communication with a conventional nurse call system 80 that is adapted to route the audio signals to the correct nurse's station, and/or other location. In some embodiments, microphone 142 acts as both a microphone and a speaker. In other embodiments, a separate speaker may be included in order to communicate the voice signals received from the remotely positioned nurse. In some embodiments, the audio communication between patient support apparatus 20 and communications outlet 74 is carried out in any of the manners, and/or includes any of the structures, disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

Fixed locator 114 also includes a location transceiver 116c and a controller 130c. Controller 130c, like controller 130b of patient support apparatus 20, controls location transceiver 116c to determine the distance and/or angular orientation between locator transceiver 116c and medical device 62, as well as, in some embodiments, the distance and/or angular orientation between location transceiver 116c and one or more of the other transceivers 116 of system 60.

After the installation of fixed locators 114 in a particular healthcare facility, the location of each fixed locator 114 is recorded. Similarly, after the installation of each headwall unit 66 in the particular healthcare facility, the location of each headwall unit 66 is recorded. The locations of headwall units 66 and fixed locators 114 are recorded in a common frame of reference (or converted to a common frame of reference after recordation). Thus, each headwall unit 66 knows its location within the healthcare facility (e.g. the room number, bay number, height and location on the headwall 72, and position and orientation relative to any nearby fixed locators 114, as well as its position and orientation relative to any nearby other headwall units 66). Similarly, each fixed locator 114 knows its location within the healthcare facility (e.g. room number, bay number, height and location on whatever wall or other structure it is attached to), as well as its position and orientation relative to any nearby other fixed locators 114 and/or headwall units 66. The term "nearby" is used to refer to locators 114 and/or headwall units 66 that are within communication range of each other, in some embodiments.

The location information of a particular fixed locator 114 may be stored in a memory onboard that particular fixed locator 114 and/or it may be stored in a memory onboard other fixed locators 114, onboard headwall units 66, and/or memory 140 of patient support apparatus 20. Similarly, the location information of a particular headwall unit 66 may be stored in a memory onboard that particular headwall unit 66 and/or it may be stored in a memory onboard other headwall units 66, onboard fixed locators 114, and/or memory 140 of patient support apparatus 20. If this location information is only stored locally (e.g. onboard the particular device whose location the information corresponds to), this location information is communicated between transceivers 116 as needed in order the transceivers 116 to determine their location relative to each other and the location of tagged medical device 62.

Tagged medical device 62 includes a tag 146 that includes a location transceiver 116d and, in at least some embodiments, a controller 130d. Tag 146, in some embodiments, may also include one or more sensors (e.g. accelerometers 118, gyroscope 132, etc., see FIG. 5) that gather data regarding the patient with whom the medical device is being used. In other embodiments, tag 146 only includes location transceiver 116d and a controller, and any other electrical components that are part of medical device 62 are positioned outside of tag 146. Regardless of the specific components contained inside or outside of tag 146, the particular data gathered by the sensors of medical device 62 may vary widely depending upon the particular medical device 62.

Although the following description of system 60 will be made primarily with respect to an embodiment in which tagged medical device 62 is an exercise device 62 (see FIGS. 7 and 8) adapted to allow a patient to exercise while seated on patient support apparatus 20, it will be understood that medical device 62 may take on other forms. It will also be understood that system 60 may be used with multiple medical devices 62 of different types, including situations where multiple medical devices 62 of different types are positioned inside of a common space volume 64 (and/or multiple medical devices 62 of the same type are positioned within a common space volume 64).

When tagged medical device 62 is implemented as an exercise device, it includes, in at least one embodiment, one or more accelerometers 118 and a gyroscope 132. Accelerometers 118 and gyroscope 132 are adapted to communicate with controller 130d. In some embodiments, exercise device 62 further includes a data transceiver 138 that is adapted to directly and wirelessly communicate with a portable device 144, such as, but not limited to, a smart phone, a tablet computer, and/or a laptop computer. In some embodiments, data transceiver 138 is a conventional Bluetooth transceiver adapted to communicate with a built-in Bluetooth transceiver positioned aboard mobile device 144. In some embodiments, exercise device 62 (or another type of medical device 62) may include, in addition to and/or in lieu of any of the aforementioned components, one or more other types of sensors, such as, but not limited to, any one or more of the following: sensors for gathering vital sign information, device usage information, diagnostic data, pharmaceutical data, movement data, sleep data, and/or still other data regarding the patient and/or the medical device 62 itself. Still further, in some embodiments, medical device 62 may include one or more redundant sensors whose outputs are utilized as checks on each other to ensure data integrity.

Controller 130d of exercise device 62, like controllers 130a, 130b, and 130c, controls location transceiver 116d to determine the distance and/or angular relationship between medical device 62 and the other location transceivers 116a, 116b, and 116c positioned within communication range. This distance and/or angular information is processed by one or more of controllers 130a-d to determine the position of tagged medical device 62, and to further determine whether it is inside or outside of volume 64. The determination of the position of tagged medical device 62 may be carried out by any of controller 130a-d, either in part or in whole. In still other embodiments, information from these transceivers 116a-d may be forwarded to a server, such as patient support apparatus server 96, and the location of medical device 62 may be calculated by server 96.

Controller 130d also processes the outputs from the one or more sensors in which it is in communication (e.g. accelerometers 118 and gyroscope 132). In some embodiments, controller 130d processes these raw outputs to determine how many repetitions (i.e. "reps") the patient has done using exercise device 62, and/or to determine other information about the usage of the exercise device 62 by the patient. Such other information may include any one or more of the following: the resistance experienced by the patient during the stroke; the estimated calories burned; the total amount of time exercised; the time per rep; the distance moved per rep, the cumulative amount of any of the aforementioned quantities (or an average or other statistical value of these quantities) for a particular patient during his or her time in the healthcare facility (e.g. the total amount of calories a patient has burned since he/she was admitted to the healthcare facility); and/or a measure of the quality of the reps. In some embodiments, one or more additional sensors may be added and/or substituted for the accelerometers and/or gyroscope, such as, but not limited to, one or more magnetometers, one or more force-measuring devices (to measure the force exerted by the patient on exercise device 62), one or more vital sign sensors (to measure the patient's breathing rate, pulse rate, and/or blood pressure), and/or still other sensors.

In some embodiments, exercise device 62 may include one or more additional sensors to detect other types of exercises besides leg presses. For example, in some embodiments, one or more sensors may be included for detecting— either in addition to or in lieu of detecting leg extensions— extensions of the patient's foot and toes against the patient contacting portion of exercise device 62. In this manner, the patient can use exercise device 62 to perform "calf raises," as well as, or in lieu of, leg extensions. In some embodiments, the movement of these calf raises may be detected by one or more of the same sensors that are used to detect the leg extensions, while in other embodiments, one or more additional sensors may be included for detecting these calf extensions.

In some embodiments, controller 130d may off-load the processing of the raw sensor outputs, either wholly or partially, to another controller, such as, but not limited to, a controller within mobile device 144, controller 130b of patient support apparatus 20, controller 130a of headwall unit 66, and/or a controller contained within patient support apparatus server 96 (or another server). When the processing of any of the data from sensors 118 and/or 132 are partially or wholly off-loaded, the routes by which the data is forwarded to the other controller(s) may be varied.

In some embodiments, exercise device 62 further includes a clock (not shown). In such embodiments, controller 130d may be adapted to use outputs from the clock to timestamp the movement of exercise device 62, and to determine any of the aforementioned quantities that involve a time component (e.g. a time when exercise with exercise device 62 commences, a time when it stops, a duration of the exercise, etc.). As was noted, in some embodiments, exercise device 62 may utilize the outputs from accelerometers 118 and/or gyroscope 132, and in some embodiments one or more additional sensors, to compute an estimated number of calories burned by the patient using exercise device 62, the amount of force exerted, the speed of movement of exercise device 62, and/or other quantities related to the usage of exercise device 62. As mentioned above, such calculations may be performed partially or wholly by controller 130d, and/or they may be sent to one or more other controllers to be performed. In some embodiments, the one or more sensors of exercise device 62 may be adapted to detect how long the patient holds a stretch or extension for (e.g. how long the leg remains extended and/or how long the calf remains flexed). In this manner, data about stretches performed by the patient can be obtained in addition to, or in lieu of, any of the aforementioned rep data.

Regardless of the specific exercise data that is gathered from exercise device 62 and its associated sensors, patient support apparatus 20 is, in at least one embodiment, adapted to display one or more components of this exercise data on one or more of the displays of patient support apparatus 20. In such embodiments, the patient support apparatus 20 receives the data from exercise device 62 via data transceiver 138 communicating with RF transceiver 136. Alternatively, the exercise data may be communicated via location transceivers 116d and 116b, or by still other means. The exercise data may also or alternatively be communicated to other recipients for processing, storage, and/or display, such as, but not limited to, one or more mobile device 144, one or more servers, one or more desktop computers, etc.

Each of location transceivers 116a, 116b, 116c, and 116d are, in at least one embodiment, ultra-wideband transceivers that are adapted to determine the aforementioned distances using time of flight, angle of arrival, and/or other characteristics of the signals exchanged between themselves. In another embodiment, each of these transceivers 116a, 116b, 116c, and 116d are Bluetooth Low Energy transceivers that are adapted to determine the distances between themselves using angle of arrival and/or channel state information. Still further, in some embodiments, location transceivers 116a-d may utilize both ultra-wideband and Bluetooth communications to determine their relative locations. In those embodiments where location transceiver 116d is a Bluetooth transceiver, or includes a Bluetooth transceiver, exercise device 62 may be modified to omit data transceiver 138 and instead use the Bluetooth transceiver 116d to communicate data directly to mobile device 144 using the built-in, conventional Bluetooth transceiver of the mobile device 144, or to any other electronic device that includes a built-in Bluetooth transceiver, such as, but not limited to, a desktop computer.

From the relative location information determined from location transceivers 116, as well as the knowledge of the position of fixed headwall unit 66 and fixed locators 114, one or more controllers are able to determine the position of exercise device 62 relative to the defined space 64. As was noted before, the one or more controllers may include any one or more of controller 130a, 130b, 130c, and/or 130d, and/or it may include a controller integrated into server 96 (or another server). When system 60 includes one or more location transceivers 116b positioned onboard patient support apparatus 20, those location transceivers 116b determine their location and/or orientation with respect to one or more off-board location transceivers 116 (e.g. 116a, 116c, and/or 116b (from other patient support apparatuses 20)), and then use this information to correlate the stationary frame of reference in which the off-board location transceivers 116 are positioned at known locations to the mobile frame of reference that is defined with respect to patient support apparatus 20 (and in which the position of patient support apparatus transceivers 116b are known). Thus, the communication between the off-board transceivers 116 and the on-board transceivers 116 enables the frame of the reference of the patient support apparatus to be determined with respect to the room's (or bay's) frame of reference, and/or vice versa.

Each of controllers 130a, 130b, 130c, and 130d may take on a variety of different forms. In the illustrated embodiment, each of these controllers is implemented as a conventional microcontroller. However, these controllers may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 130a, 130b, 130c, and 130d when carrying out the functions described herein, as well as the data necessary for carrying out these functions, are stored in a corresponding memory that is accessible to that particular controller 130a, 130b, 130c, and 130d. In some embodiments, one or more of the controllers 130a-d are separate from the conventional ultra-wideband modules discussed above that are available from different companies, while in other embodiments, one or more of the controllers 130a-d are integrated into one or more of these conventional ultra-wideband modules.

Figure 6:
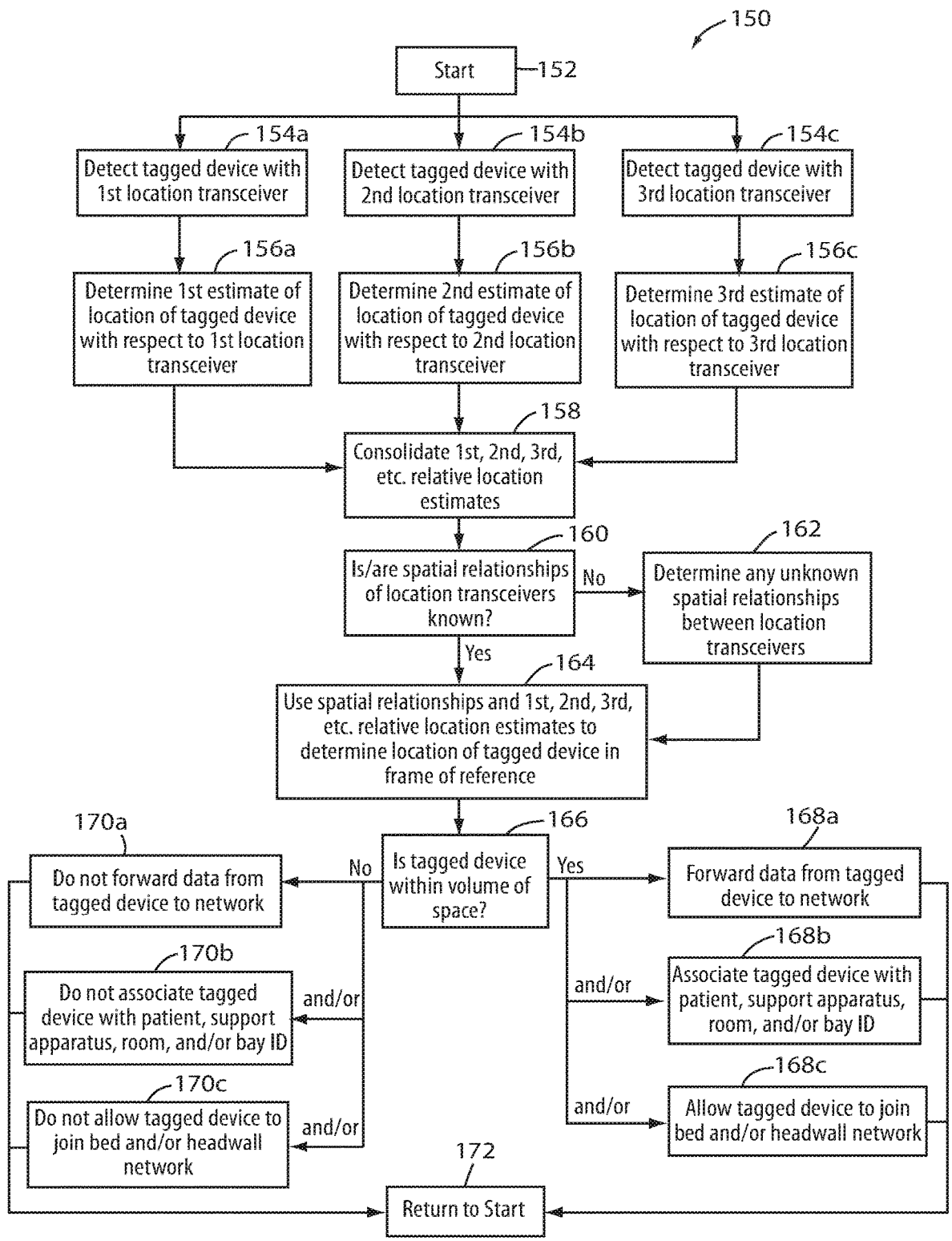
FIG. 6 is a flow diagram of an algorithm implemented by at least one embodiment of the system for automatically detecting the position of tagged medical devices.

FIG. 6 illustrates one example of a control algorithm 150 followed by system 60. Control algorithm 150 may be carried out by any one or more of controllers 130a-d and/or a controller integrated into one or more servers (e.g. server 96). Thus, it will be understood that the "controller" referenced in algorithm 150 may refer to any one or more of these controllers, and that the term "controller 130," as used herein, generically refers to any one or more of these controllers.

Algorithm 150 starts at an initial step 152. Although step 152 is identified as a "start" step, it will be understood that, at least in some embodiments, algorithm 150 is continuously and repetitively operating. By continuously and repetitively operating, algorithm 150 is able to automatically detect the presence of a tagged exercise device 62 whenever the tagged exercise device 62 is moved into range of the various location transceivers 116. Because of this automatic detection, it is not necessary for an individual to take any specific step to initiate algorithm 150, or to take any step to have system 60 automatically detect the presence of tagged exercise device 62.

After step 152 (FIG. 6), controller 130 moves to step 154, which comprises sub-steps 154a-c. At each of the sub-steps 154a-c, the presence of the tagged exercise device 62 is detected by each of the location transceivers 116 that are within range of the tagged exercise device 62 and that are part of system 60. System 60 may include different numbers of location transceivers 116, and the number of sub-steps of step 154 of algorithm 150 may therefore vary from the three shown in FIG. 6. In other words, although FIG. 6 shows three sub-steps 154a-c, it will be understood that, in some situations and/or in some other embodiments, algorithm 150 may include four sub-steps 154a-d, or five sub-steps 154a-e, or two sub-steps 154a-b, a single sub-step 154a, etc. That is, the number of sub-steps of step 154 varies in accordance with the number of location transceivers 116 that are able to, and adapted to, detect the location of a tagged exercise device 62 at its current location within the healthcare facility.

In the example shown in FIG. 6, there are three location transceivers 116 that detect the presence of the tagged exercise device 62 at step 154 (sub-steps 154a-c). The position of these three location transceivers 116 may vary from embodiment to embodiment, as will be discussed in greater detail below. For example, in some embodiments, two of the locations transceivers 116 will be integrated into patient support apparatus 20 (i.e. location transceivers 116b), and another one will be integrated into a nearby headwall unit 66 (i.e. location transceiver 116a). In other embodiments, there may be only a single location transceiver 116b onboard patient support apparatus 20, another location transceiver 116a integrated into a headwall unit 66, and another location transceiver 116c integrated into a stationary locator 114. Still other combinations are possible.

Sub-steps 154a-c are carried out using ultra-wideband signals and/or Bluetooth signals. In some embodiments, each location transceiver 116 is configured to repetitively send out interrogation signals to any tagged exercise device 62 that is within range of these transceivers 116. Sub-steps 154a-c occur when the tagged exercise device 62 moves within range of these transceivers 116 and responds to these interrogation messages.

At sub-steps 156a-c, each location transceiver 116 determines a location estimate of the tagged exercise device 62 with respect to itself. Thus, as with sub-steps 154a-c, the number of sub-steps of step 156 will vary according to the number of location transceivers 116 that are implemented in system 60 (or within a particular room or other area of system 60). It will therefore be understood that algorithm 150 may include more than, or less than, the three sub-steps 156a-c of step 156, depending upon the particular embodiment and/or implementation within a particular area of system 60.

At sub-steps 156a-c, the transceivers 116a-c that are not part of tagged exercise device 62 send signals back and forth to the location transceiver 116d that is part of the tagged exercise device 62. The transceivers 116a-d and their respective controllers 130 use these signals to determine relative position estimates between the tagged exercise device 62 and each one of the other location transceivers 116a-c. Thus, for example, at sub-step 156a, a first position estimate of tagged exercise device 62 with respect to a first location transceiver 116a positioned on headwall unit 66 is obtained. Continuing with this example, at sub-step 156b, a second position estimate of tagged exercise device 62 with respect to a second location transceiver 116b positioned onboard patient support apparatus 20 is obtained. Continuing further with this example, at sub-step 156c, a third position estimate of tagged medical device with respect to a third location transceiver 116b also position onboard patient support apparatus 20 is obtained. In different examples, the position estimates may correspond to relative position estimates made with respect to different locations (e.g. a position estimate of exercise device 62 with respect to a location transceiver 116c positioned on a stationary locator 114, etc.).

After the relative position estimates of sub-steps 156a-c are made, the results of each of these position estimates are shared with at least one common controller amongst the various controllers 130a-d (or with a controller onboard one or more servers) at step 158. This sharing may take place by transmitting the position estimates via location transceivers 116. That is, location transceivers 116 are not only able to determine the relative positions between each other, but they are also able to transmit data to and from each other. By sharing the position estimates, the common controller is able to combine the different position estimates to generate a single position estimate that is more precise and more accurate than each of the individual position estimates alone. Before combining those position estimates, however, the common controller moves to step 160 where it determines if the relative position of all of the location transceivers 116 (other than the location transceiver 116d on exercise device 62) are known or not. If they are known, it moves to step 164. If they are not known, it moves to step 162.

At step 162, the unknown relative positions of each and every one of the location transceivers 116 that were used in sub-steps 154a-c (and 156a-d) are determined. In general, step 162 will only be carried out between location transceivers 116 that are mobile (e.g. location transceivers 116b positioned onboard patient support apparatus 20) and the location transceivers 116 (e.g. 116a, 116c) that are stationary. This is because the relative positions of the stationary location transceivers 116a, c are fixed and determined during the installation of system 60, and are recorded in one or more memories that are accessible to the common controller. For example, the relative position of a location transceiver 116a positioned in a headwall unit 66 with respect to a location transceiver 116c positioned in a stationary locator 114 that is within range of that headwall unit 66 is determined during system installation and stored in memory. It is therefore unnecessary to determine this relative position at step 164 because it is already known. The position of the location transceiver 116a within the headwall unit 66 with respect to a location transceiver 116b onboard patient support apparatus 20, as one example, however, will not be known because patient support apparatus 20 is mobile and this relative position can change at any time. Controller 130 therefore determines this relative position at step 162 and forwards the results to the common controller.

At step 162 (FIG. 6), controller 130 therefore determines the relative position of each of the location transceivers 116b onboard patient support apparatus 20 with respect to each of the in-range off-board location transceivers 116a, 116c. If there are two or more location transceivers 116b onboard patient support apparatus 20, it is not necessary for the controller 130 to determine the relative position of these transceivers 116b because this information is determined during the manufacture of patient support apparatus 20 and stored in memory 140 (and shared with the common controller, as appropriate). All of the relative position estimates that are made at step 162 are forwarded thereafter to the common controller.

At step 164, the common controller combines all of the information from each of the positions estimates received at step 158 and 162, as well as the known information of the spatial relationships between the off-board location transceivers 116a, 116c (if there are more than one of these), as well as the known information of the spatial relationships between the on-board location transceivers 116b (if there are more than one of these) to generate a single position estimate of the tagged medical device within a suitable frame of reference. This combination of position estimate data and known spatial relationship data may be carried out using mathematical techniques that are known to a person skilled in the art, such as, but not limited to, trilateration and/or triangulation.

For example, in some embodiments, each position estimate of tagged exercise device 62 with respect to location transceiver 116a, b, or c may generate a distance estimate between the device 62 and each transceiver 116. A single distance estimate may further translate into a position estimate corresponding to a sphere of possible locations of exercise device 62 with respect to a single transceiver 116. By combining multiple of the spheres together from different location transceivers 116, the intersection of these multiple spheres can be determined so as to generate a single and more accurate position estimate of the tagged exercise device 62. Different and/or more refined mathematical techniques may also or alternatively be used that utilize angular information derived from the relative positions between each transceiver 116 and the tagged exercise device 62.

The result of step 164 (FIG. 6) is an estimate of the current position of exercise device 62 within a known frame of reference. As was alluded to earlier, this frame of reference may be a stationary frame of reference (e.g. one that is fixed with respect to the room or other location within the healthcare facility) or it may be a mobile frame of reference (e.g. one that moves with the patient support apparatus 20). In some embodiments, a stationary frame of reference is utilized by system 60 if the space volume 64 is stationary, while in other embodiments, a mobile frame of reference is utilized by system 60 if the space volume 64 moves with patient support apparatus 20. In either case, controller 130 is able to combine the position information at step 164 into a common frame of reference by using the known (or measured) positions between those location transceivers 116 that are positioned off-board patient support apparatus 20 and those location transceivers 116 that are position onboard patient support apparatus 20.

After completing step 164, controller 130 determines if the current position estimate of tagged exercise device 62 is inside the volume of space 64 or outside the volume of space 64. This is done by consulting one or more memories (e.g. memory 140 of patient support apparatus 20, or a memory stored in a server of LAN 90, or another memory) that store the data defining the boundary of space volume 64 and/or the criteria used to define this boundary. If controller 130 determines that tagged exercise device 62 is positioned inside space volume 64 at step 166, it performs one or more of steps 168a, b, and/or c. If controller 130 determines at step 166 that tagged exercise device 62 is positioned outside of space volume 64, it performs one or more of steps 170a, 170b, and/or 170c.

At step 168a, controller 130 forwards data received from tagged exercise device 62 to local area network 90 (such as patient support apparatus server 96, which may then forward the data elsewhere, such as, but not limited to, an electronic medical record server). This data may be forwarded at step 168a in a variety of different manners. In one embodiment, once a tagged exercise device 62 is determined to be within space volume 64, it may send data to patient support apparatus 20 (via location transceivers 116d and 116b, or via a separate set of transceivers) and controller 130b will then forward this data to network 90 via its onboard network transceiver 92 at step 168a. In another embodiment, once a tagged exercise device 62 is determined to be within space volume 64, it may send data to headwall unit 66 and headwall unit controller 130a will then forward this data to network 90 via its own onboard network transceiver (not shown) at step 168a. In still other embodiments, stationary locators 114 may include their own network transceivers and the tagged exercise device 62 may forward its data to one or more of these locators 114, which then forward the data network 90. In still other embodiments, patient support apparatus 20 and/or headwall unit 66 may initiate communication with the tagged exercise device 62 at step 168a using a transceiver of a different type than location transceivers 116 (e.g. data transceiver 138), at which point data is forwarded using that different type of transceiver to either patient support apparatus 20 or headwall unit 66, and the recipient of that data then forwards it to network 90. Still other data routes are possible.

In addition to, or as an alternative to, forwarding data at step 168a (FIG. 6), controller 130 may react to the determination of exercise device 62 being inside space volume 64 by associating the tagged device with the patient assigned to patient support apparatus 20 (or a proxy for that patient), as set forth in step 168b. In other words, at step 168b, controller 130 determines that, because the tagged exercise device 62 is within the space volume 64, it is to be associated with that particular patient (or his or her proxy). This association may be carried out by controller 130 at step 168b in a variety of different manners. In one manner, controller 130a of headwall unit 66 and/or controller 130b of patient support apparatus 20 sends a message to patient support apparatus server 96 that includes a unique identifier of the exercise device 62 along with a unique identifier of patient support apparatus 20 and/or a unique identifier of headwall unit 66. By sending the unique identifier of the exercise device 62 with a unique identifier of the patient support apparatus 20 and/or headwall unit 66, server 96 recognizes that the exercise device 62 is to be associated with that particular patient support apparatus 20 and/or headwall unit 66. Further, because server 96 knows the location of patient support apparatus 20 and headwall unit 66, it is able to consult a data table correlating that location to a particular patient. This data table may be stored in another server of network 90, such as, but not limited to, an Admission, Discharge, and Transfer (ADT) server, or still another type of server. Further details of how system 60 may associate a unique patient support apparatus identifier and/or a unique headwall unit identifier with a patient, a room, and/or bay are disclosed in commonly assigned U.S. patent application Ser. No. 16/832,760 filed Mar. 27, 2020, by inventors Thomas Durlach et al. and entitled PATIENT CARE SYSTEM, and/or commonly assigned PCT patent application serial number PCT/US2020/039587 filed Jun. 25, 2020, by inventors Thomas Durlach et al. and entitled CAREGIVER ASSISTANCE SYSTEM, the complete disclosures of both of which are incorporated herein by reference. Still other manners of associated exercise device 62 to a particular patient also or alternatively be used at step 168b.

At step 168c, controller 130 allows tagged exercise device 62 to join a network of electronic devices positioned within the vicinity of patient support apparatus 20 and/or headwall unit 66. The network includes patient support apparatus 20, the adjacent headwall unit 66, and/or one or more other medical devices 62 that are positioned within space volume 64. In some embodiments, to join this communication network, the tagged exercise device 62 must be granted permission rights, such as an access key, or other authorization information, that allows it to join the network. Once joined, tagged exercise device 62 is able to communicate data to and from these devices as part of a separate communication network. In some embodiments, the network that system 60 allows exercise device 62 to join at step 168c is one or more of the mesh networks disclosed in commonly assigned U.S. patent application Ser. No. 16/569,225 filed Sep. 12, 2019, by inventors Alexander Bodurka et al. and entitled PATIENT SUPPORT APPARATUS COMMUNICATION SYSTEMS, the complete disclosure of which is incorporated herein by reference. System 60 may allow exercise device 62 access to still other types of networks at step 168c.

As was noted before, controller 130 may perform any one or more of steps 168a, 168b, and/or 168c as a result of determining that the exercise device 62 is positioned within the space volume 64. It will, of course, be understood that system 60 may take one or more additional actions as well. After completing whichever actions it takes as part of step 168, controller 130 moves to step 172 and re-starts algorithm 150, as will be discussed in greater detail below.

If controller 130 determines at step 166 (FIG. 6) that the tagged exercise device 62 is not positioned inside of space volume 64, it proceeds to perform any one or more of steps 170a, 170b, and/or 170c, depending upon the particular embodiment of system 60. Steps 170a, 170b, and 170c are, in essence, the opposite of steps 168a, 168b, and 168c, respectively. Thus, if controller 130 performs steps 170a, it does not forward (or stops forwarding if it was previously forwarding) data from tagged exercise device 62 to server 96 and/or another server on network 90. Similarly, if controller 130 performs step 170b, it does not associate (or stops associating if it was previously associating) tagged exercise device 62 with the adjacent patient support apparatus 20 (or the patient assigned to that particular patient support apparatus 20, room, and/or bay). And if controller 130 performs step 170c, it does not allow (or stops allowing if it was previously allowing) the tagged exercise device 62 to join the wireless network mentioned above with respect to step 168c.

After completing whichever ones of steps 170a-c that system 60 is configured to perform, it moves to step 172 where it returns to start step 152. System 60 then re-performs the steps of algorithm 150 and continues doing so until it is manually terminated. In some embodiments, the frequency at which system 60 cycles through algorithm 150 may be on the order of once a minute, once a second, or multiple times a second. In some embodiments, this frequency or periodicity remains the same throughout the operation of system 60 (i.e. it is static). In other embodiments, system 60 may vary the periodicity of algorithm 150 based upon one or more factors, such as, but not limited to, the presence or absence of one or more tagged medical devices 62 within space volume 64, the number of devices 62 within space volume 64, whether movement of one or more tagged device 62 is detected, the proximity of one or more of the exercise device 62 to the borders of the space volume 64, the proximity of one or more of the medical devices 62 to another patient support apparatus 20, the particular room and/or bay in which the patient support apparatus is located, the time of day, etc.

It will be understood that, although system 60 and algorithm 150 have been primarily described herein as pertaining to determining the location of one or more tagged exercise devices 62 (or other types of tagged medical devices 62) with respect to a particular patient support apparatus 20, system 60 may be implemented in multiple rooms and/or multiple locations within a healthcare facility for multiple patient support apparatuses 20. Thus, for example, system 60 may include multiple patient support apparatuses 20, multiple space volumes 64 (for each of the rooms, bays, and/or patient support apparatuses), and multiple sets of headwall units 66 and, in some embodiments, multiple fixed locators 114. System 60 may therefore, at any given time, be monitoring the position of one or more medical devices 62 with respect to a first volume 64 and a first patient support apparatus 20 while also monitoring the positions of one or more other medical devices 62 with respect to other patient support apparatuses 20 and their respective space volumes 64.

Although FIG. 4 illustrates an embodiment of system 60 that includes a single location transceiver 116a integrated into headwall unit 66, a single location transceiver 116b integrated into patient support apparatus 20, and a single location transceiver 116c integrated into stationary locator 114, it will be understood by those skilled in the art that this arrangement may be varied considerably. Thus, for example, one or more of these location transceivers 116 may be omitted or duplicated (or included in triplicate, or still larger numbers). Still further, one or more additional location transceivers 116a positioned inside nearby headwall units 66, and/or one or more additional location transceivers 116b positioned inside one or more nearby patient support apparatuses 20 may also and/or alternatively be utilized in combination with any of the location transceivers shown in FIG. 4. In general, the components, operation, and layout of system 60 may take on a wide variety of different forms, including, but not limited to, any of the embodiments disclosed in commonly assigned U.S. patent application Ser. No. 63/154,677 filed Feb. 27, 2021, by inventors Celso Pereira et al. and entitled SYSTEM FOR DETERMINING PATIENT SUPPORT APPARATUS AND MEDICAL DEVICE LOCATION, the complete disclosure of which is incorporated herein by reference.

In some embodiments, one or more of the location transceivers 116 disclosed herein may use one or more conventional beamforming techniques to narrow the range over which they are able to communicate, thereby allowing a finer granularity in the position of medical device 62 (or any other location transceiver 116) to be determined. Further details of the beamforming techniques that may be implemented into one or more embodiments of system 60 are described in the aforementioned '677 application, which has already been incorporated herein by reference.

In some embodiments, headwall unit 66 and/or patient support apparatus 20 may use beamforming techniques that vary depending upon which particular device these structures are communicating with. For example, when the location transceiver(s) 116a of headwall unit 66 communicate with the location transceiver(s) 116b of patient support apparatus 20, these location transceivers 116a, b may use a first beamforming technique. When either of these sets of transceivers 116a or 116b communicates with the tagged exercise device 62, they may use a second and different beamforming technique. These different beamforming techniques create better spatial sensitivity regarding the potential location of the device 62 with which the location transceiver 116a or 116b is communicating, as well as better spatial sensitivity regarding the position of patient support apparatus 20 relative to headwall unit 66, both of which allow a more refined estimate of the position of device 62 to be determined.

In any of the various embodiments of system 60, controller 130 may be adapted to generate additional information about the position and orientation of patient support apparatus 20 with respect to headwall unit 66 via its communication with the infrared transceiver 120 of headwall unit 66. That is, the infrared transceiver 120 of headwall unit 66 is configured to only be able to successfully communicate with the infrared transceiver 134 of patient support apparatus 20 if head end 38 of patient support apparatus 20 is positioned generally in front of and facing headwall unit 66. This is because IR transceiver 134 of patient support apparatus 20 is attached to the head end of patient support apparatus 20 and because these IR communications rely on an unobstructed line of sight pathway between headwall unit 66 and patient support apparatus 20. Thus, controller 130*b* is able to determine from its successful communication with IR transceiver 120 that its head end is oriented toward headwall 72 (to which headwall unit 66 is mounted), and that it is within the relatively short communication range of headwall unit 66 (e.g. on the order of five to ten feet). This position and orientation information may be combined with the position information obtained from the other location transceivers 116 (e.g. 116*a* of headwall unit 66 and/or 116*c* of stationary locator 114) to determine the location of a tagged exercise device 62 relative to a space volume 64.

In any of the various embodiments of system 60, controller 130 may also be adapted to generate additional information about the position of patient support apparatus 20 and/or exercise device 62 with respect to one or more other patient support apparatuses 20 that have location transceivers 116*b* that are positioned within communication range. That is, if system 60 determines a location and/or orientation of a first patient support apparatus 20 with respect to a particular room (or other landmark within the healthcare facility), system 60 may have the location transceivers 116*b* aboard the first patient support apparatus 20 communicate with a tagged medical device 62 positioned adjacent a second patient support apparatus 20, and/or communicate with one or more location transceivers 116*b* positioned aboard the second patient support apparatus 20. This communication provides additional estimates of the position of the tagged exercise device 62 and/or second patient support apparatus 20, and therefore may be able to provide a more accurate estimate of the position of the tagged exercise device 62 vis-a-vis its respective space volume 64.

It will be understood by those skilled in the art that any of the different configurations and/or embodiments of system 60 that are described herein may be combined, either wholly or partially, with each other. Some of the combinations may take place throughout an entire healthcare facility, while others of these combinations may take place in only an individual room and/or in other locations. Thus, for example, in some embodiments, some rooms of a particular healthcare facility may include two headwall units 66 as well as, say, a stationary locator 114; while other rooms of the same healthcare facility may include two stationary locators 114 positioned on a first wall in the room and another stationary locator 114 positioned on a second wall of the room. As another example, in some embodiments, some patient support apparatuses 20 may include different numbers of location transceivers 116*b* than other patient support apparatuses 20 located within that same facility. For example, a particular healthcare facility may include some patient support apparatuses 20 having no location transceivers 116*b* and other patient support apparatuses 20 having one or two location transceivers 116*b*. Still other variations and combinations of any of the features and/or functions of the various embodiments of system 60 may be implemented.

Figure 7:
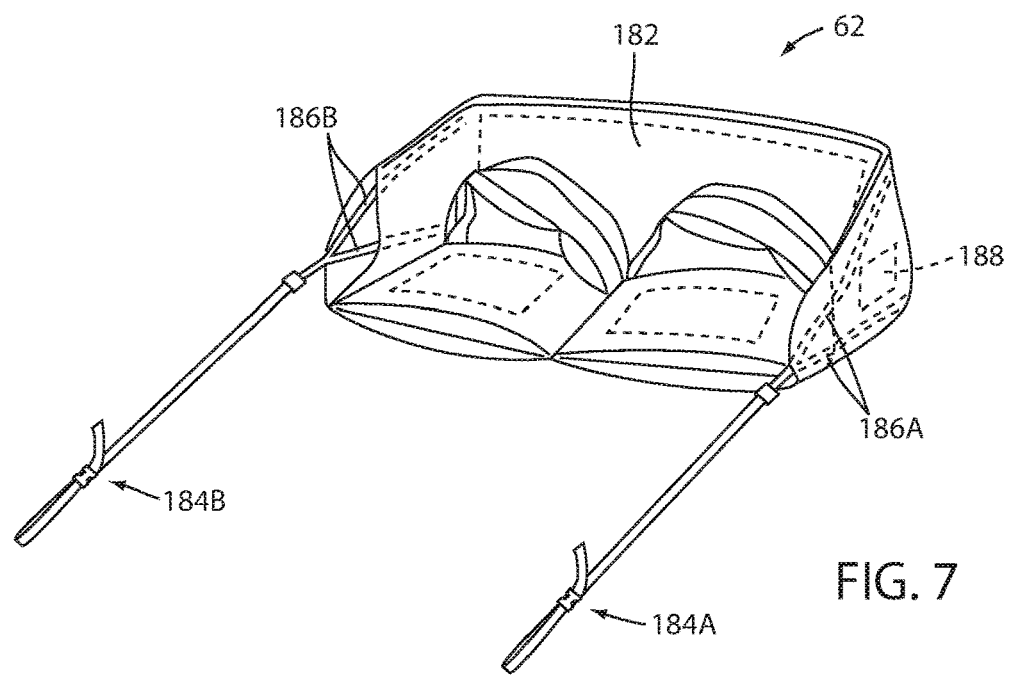
FIG. 7 is a perspective view of a tagged exercise device whose position may be detected by the system of FIG. 4.
Figure 8:
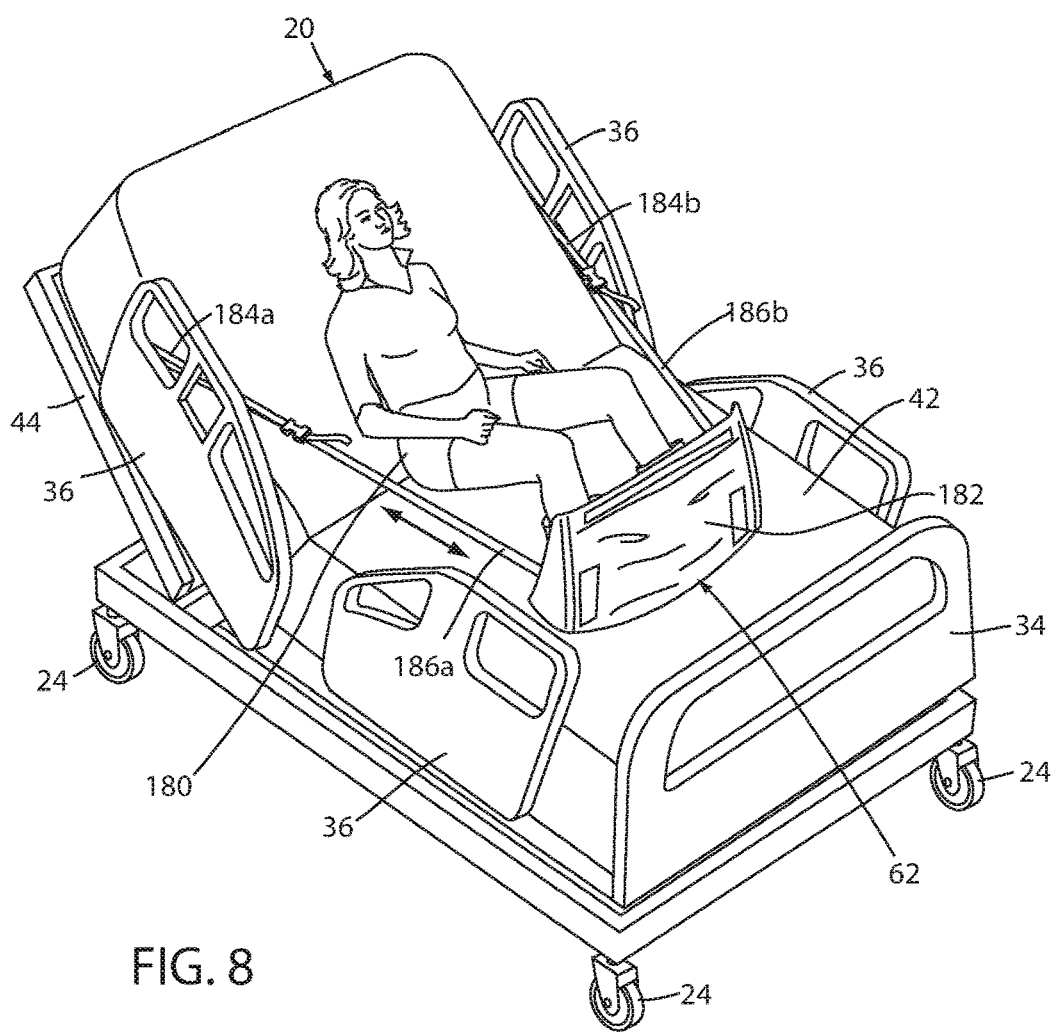
FIG. 8 is a perspective view of the exercise device of FIG. 7 shown coupled to a patient support apparatus.

FIGS. 7 & 8 illustrate one embodiment of an exercise device 62 that may be used with, and whose location may be detected by, system 60. Exercise device 62 is designed to exercise the legs of a patient 180 positioned on patient support apparatus 20 (FIG. 8). More particularly, exercise device 62 is adapted to allow a patient 180 to perform leg presses in which the patient's legs must overcome resistance offered by exercise device 62 when the patient's legs move from a first position (shown in FIG. 8) in which the patient's knees are bent to a second position (not shown) in which the patient's legs are substantially straight (i.e. knees not bent, or not bent as much).

As shown in FIGS. 7 and 8, exercise device 62 includes a patient-contacting portion 182, a pair of connectors 184*a, b*, a pair of elastic portions 186*a, b*, and one or more electronic housings 188 (FIG. 7). Patient-contacting portion generally extends between elastic portions 186*a*, 186*b* and defines an area where the patient's feet are able to contact exercise device 62. Thus, patient-contacting portion 182 forms a foot pad for the patient's feet. Elastic portions 186*a* and 186*b* are designed to stretch and retract such that foot-contacting portion 182 is able to be moved between a retracted position (patient's knees are bent) shown in FIG. 8 and an extended position (not shown) in which the patient's legs are generally straight.

Connectors 184*a* and 184*b* are designed to releasable couple to patient support apparatus 20. In the illustrated embodiment, connectors 184*a*-*b* are designed to be fastened to the head end siderails 36. It will be understood, however, that connectors 184*a*-*b* may be designed to attach to other locations on patient support apparatus 20. Still further, it will be understood that the design of connectors 184*a*-*b* may be modified substantially from what is shown in FIGS. 7-8 to include different structures for releasably coupling exercise device 62 to patient support apparatus 20. In some embodiments, exercise device 62 includes any one or more of the same structure(s), components, and/or functionality of the bed exercise systems disclosed in the following commonly assigned documents: U.S. provisional patent application Ser. No. 63/129,691 filed Dec. 23, 2020, by inventors Kaitlin Konopacz et al. and entitled BED EXERCISE SYSTEMS AND METHODS; U.S. non-provisional patent application Ser. No. 17/334,306 filed May 28, 2021, by inventors Kaitlin Konopacz et al. and entitled BED EXERCISE SYSTEMS AND METHODS; U.S. provisional patent application Ser. No. 63/223,841 filed Jul. 20, 2021, and entitled BED EXERCISE SYSTEMS AND METHODS; U.S. provisional patent application Ser. No. 63/242,272 filed Sep. 9, 2021, and entitled BED EXERCISE SYSTEMS AND METHODS; and U.S. provisional patent application Ser. No. 63/257,535 filed Oct. 19, 2021, and entitled BED EXERCISE SYSTEMS AND METHODS, the complete disclosures of all of which are incorporated herein by reference.

Although elastic portions 186*a, b* provide resistance when the foot-contacting portion 182 is moved from the retracted position to the extended position, it will be understood that other means for resisting movement of the patient's legs may be implemented. Such other means include, but are not necessarily limited to, springs, weights, and/or materials that resist compression. In addition, although connectors 184*a, b* are shown in the accompanying drawings as being physically attached to siderails 36, it will be understood by those skilled in the art that exercise device 62, in some modified embodiments, could be constructed to merely rest on, or be supported by, patient support apparatus 20, rather than being physically attached thereto. Thus, as one example, a cross bar (not shown) that extends laterally across patient support apparatus 20 (e.g. from within one opening in a first siderail 36 to another opening in a second siderail 36 positioned laterally across from the first siderail 36) could be used to support elastic portions 186a, b instead of connectors 184a, b. Still other types of couplings could be used.

Electronic housing 188 (FIG. 7) houses the electronics that are incorporated into exercise device 62. As was described above with respect to FIG. 5, these electronics include a location transceiver 116d, a controller 130d, a plurality of accelerometers 118, a data transceiver 138, and a gyroscope 132. In some embodiments, electronic housing 188 may also include one or more batteries (not shown) to provide power to these electronic components. It will be understood that electronic housing 188 may include different sets of electronics in different embodiments, and that in some embodiments, multiple electronic housings 188 may be included that house different ones of the aforementioned set of electronic components (or subsets of this set). For example, in some embodiments, a first housing includes location transceiver 116d and as associated controller, while a second housing includes data transceiver 138 and one or more sensors (such as accelerometers 118 and/or gyroscope 132). As another example, in some embodiments, exercise device 62 omits gyroscope 132 and/or data transceiver 138, in which case housing 188 only houses the other electronics shown in FIG. 5. Still other variations are possible.

In some embodiments, gyroscope 132, accelerometers 118, and data transceiver 138 may be implemented as an SLTB010A EFR32BG22 Thunderboard Kit commercially available from Silicon Labs of Austin, Tex. In such embodiments, electronic housing 188 may include additional electronic components that are included as part of this kit, such as, but not limited to, one or more humidity sensors, light sensors, magnetometers, and/or other sensors. In other embodiments, a modified version of this kit may be used to implement accelerometers 118, data transceiver 138, and gyroscope 132, such as a version that omits one or more of these additional sensors (e.g. the humidity, light, and/or other sensors). In still other embodiments, gyroscope 132, accelerometers 118, and data transceiver may be implemented without using the aforementioned kit. And still further, as mentioned above, in some embodiments, gyroscope 132 may be omitted altogether from exercise device 62.

In those embodiments of exercise device 62 that include the aforementioned Thunderboard kit, exercise device 62 may be constructed to include two separate controllers that are in communication—a first controller that is included as part of the Thunderboard kit and a second controller that is included within any one of the aforementioned location modules (e.g. the Trimension™ ultra-wideband SR150, SR100T, SR040, NCJ29D5, and/or OL23DO modules available from NXP Semiconductors of Austin, Tex.) In still other embodiments, the electronics from the Thunderboard kit may be combined with the electronics from the location module. Still other variations are possible.

In at least one embodiment, housing 188 is positioned along an end of foot-contacting portion 182, such as is shown in FIG. 7, rather than in the middle of foot-contacting portion 182. This position helps ensure that the accelerations experienced by (and detected by) the three mutually orthogonal accelerometers 118 are stronger. Such stronger signals may results from the housing 188 not only translating back and forth in a single direction as the patient exercises, but also from the housing 188 rotating about a generally vertical axis as the patient moves the exercise device 62 between the extended and retracted position. Regardless of the specific position of housing 188, the accelerations are detected when the exercise device 62 is moved between the extended and retracted positions. By choosing a location on device 62 that yields stronger acceleration signals, controller 130d is able to more easily analyze the signals, which in turn enables the number of reps, and/or other information, to be more reliably and/or more easily determined from these sensor outputs. It will be understood that accelerometers 118 may be positioned at locations other than what is shown in FIG. 7, including, but not limited to, a middle area of foot-contacting portion 182 (between elastic portions 186a, b).

Controller 130 is adapted to automatically detect when exercise device 62 is coupled to patient support apparatus 20 by determining the location of exercise device 62 relative to space volume 64 in the manner described above in algorithm 150 (or a variation or algorithm 150). In at least one embodiment, controller 130 does this by concluding that exercise device 62 is coupled to the patient support apparatus 20 when exercise device 62 is positioned within space volume 64 and concluding that exercise device 62 is not coupled to patient support apparatus 20 when exercise device 62 is positioned outside of space volume 64. In alternative embodiments, exercise device 62 and/or patient support apparatus 20 may include one or more additional sensors for automatically detecting the presence of exercise device 62.

In response to controller 130 detecting that exercise device 62 is positioned within space volume 64, it is configured in some embodiments to perform one or more steps that are in addition to, and/or in lieu of, the sub-steps 168a-c of algorithm 150. In some embodiments, these steps include sending a message to a patient support apparatus server 96 indicating that exercise device 62 is now associated with patient support apparatus 20. This message includes a unique ID of the patient support apparatus 20 and a unique ID of the exercise device. In some embodiments, the unique ID of the headwall unit 66 (which provides location information due to it being mounted in a fixed and known location within the healthcare facility) that patient support apparatus 20 is currently adjacent to may also be sent to patient support apparatus server 96.

In addition to, or in lieu of, sending this message, controller 130 may be configured to perform an automatic pairing operation in response to detecting that exercise device 62 is positioned with space volume 64. This automatic pairing pairs data transceiver 138 with another wireless transceiver, such as RF transceiver 136 of patient support apparatus 20 and/or RF transceiver 122 of the headwall unit 66 adjacent to patient support apparatus 20. This automatic pairing takes place, in some embodiments, by exercise device 62 communicating the unique ID of the exercise device 62 to patient support apparatus 20 and/or headwall unit 66 via its location transceiver 116d. This unique ID is used by the patient support apparatus 20 and/or headwall unit 66 to automatically pair transceivers 136 and/or 122 with data transceiver 138. In other words, after exercise device 62 is determined to be positioned with space volume 64, either or both of controllers 130b and/or 130a are configured to automatically allow pairing between their respective RF transceiver 122, 136 and data transceiver 138. This is accomplished through the use of the exercise device's unique ID, as explained below.

Turning first to the case of automatic pairing with patient support apparatus 20, when controller 130 determines that exercise device 62 is positioned within space volume 64, this fact is communicated to controller 130b (to the extent this determination wasn't made by controller 130b). This communication may take place via communication between location transceiver 116b and any of the other location transceivers 116, and/or it may take place via one or more other transceivers (e.g. 134, 136, and/or 92). Once controller 130b is apprised of the fact that exercise device 62 is positioned within space volume 64, as well as the unique ID of that exercise device 62, it instructs RF transceiver 136 to automatically establish a communication link with data transceiver 138. RF transceiver 136 uses the unique ID to ensure that it communicates only with the exercise device 62 that is positioned within space volume 64, and not some other in-range device that is capable of RF communication. Thus, either data transceiver 138 sends a request to pair with RF transceiver 136 that includes the unique ID of exercise device 62, or RF transceiver 136 sends a request to pair with data transceiver 138 that includes the unique ID. In the former case, controller 130b allows RF transceiver 136 to pair with data transceiver 138 because the request message includes the unique ID of the exercise device 62 that is positioned within space volume 64 (if it did not, it would not allow such pairing). In the latter case, the unique ID is used as a form of address such that the request for pairing sent from RF transceiver 136 is addressed specifically to the data transceiver 138 of the exercise device 62 positioned within space volume 64. In either of these manners, the pairing takes place automatically and in a manner that prevents RF transceiver 136 from pairing with some other RF-enabled device that is not exercise device 62 but is otherwise positioned within communication range of RF transceivers 136 and/or 138.

To the extent headwall unit 66 is configured to automatically pair with data transceiver 138 (which it may or may not be in different embodiments), it is carried out by controller 130a and RF transceiver 122 in the same manner described above for patient support apparatus 20. Thus, in at least some embodiments, system 60 is configured to automatically pair data transceiver 138 with one or both of RF transceivers 122, 136 when exercise device 62 is positioned within space volume 64. This automatic pairing takes place without requiring any manual pairing steps on the part of the user. Thus, for example, the user is not required to input any information into any of the control panels 54 of patient support apparatus; press any button or switches on patient support apparatus 20, headwall unit 66, and/or exercise device 62 itself; or take any other action that specifies which exercise device 62 patient support apparatus 20 and/or headwall unit 66 is supposed to pair with. Instead, system 60 automatically pairs with the exercise device 62 within space volume 64 and does so in a manner that excludes any automatic pairing with any RF enabled devices that are positioned outside of space volume 64 but within communication range. As was noted previously, transceivers 138, 136, and 122 may be conventional Bluetooth or Bluetooth Low Energy transceivers in some embodiments.

Once transceiver 138 of exercise device 62 is paired with patient support apparatus 20 and/or headwall unit 66, it is adapted to transmit movement data generated from accelerometers 118 and/or gyroscope 132 and/or other data to those devices. In some embodiments, patient support apparatus 20 is configured to display the transmitted data on a display of patient support apparatus 20. In other embodiments, patient support apparatus 20 does not display this transmitted data. Whether exercise device 62 transmits data to patient support apparatus 20 or headwall unit 66, the recipient is configured to forward the transmitted data to a server on local area network 90. When forwarding this data to a server, patient support apparatus 20 and/or headwall unit 66 include a unique identifier that uniquely identifies themselves and that distinguishes themselves from other patient support apparatuses 20 and/or headwall units 66 that may be present within the same healthcare facility. The recipient server, which may be patient support apparatus server 96, uses the unique identifier of the patient support apparatus 20 and/or headwall unit 66 to determine which room, bay, and/or patient exercise device 62 is associated with. Further details by which patient support apparatus server 96 is able to determine which patient, room, or bay that messages from a patient support apparatus 20 (or headwall unit 66) are associated with are disclosed in the aforementioned commonly assigned U.S. patent application Ser. No. 16/832,760 filed Mar. 27, 2020, by inventors Thomas Durlach et al. and entitled PATIENT CARE SYSTEM, and/or commonly assigned PCT patent application serial number PCT/US2020/039587 filed Jun. 25, 2020, by inventors Thomas Durlach et al. and entitled CAREGIVER ASSISTANCE SYSTEM, the complete disclosures of both of which have been incorporated herein by reference.

If patient support apparatus 20 determines the room and/or bay with which exercise device 62 is associated (i.e. which room or bay it is currently positioned in), it may be configured in some embodiments to use this information to also determine the specific patient that exercise device 62 is associated with, such as by consulting one or more servers on network 90 that store information correlating rooms and/or bays to patients. Once the patient ID is determined, patient support apparatus server 96 may be configured to forward the data from exercise device 62 to an electronic medical records server on network 90 with instructions to store the data in that particular patient's electronic medical record. Alternatively, or additionally, patient support apparatus server 96 may send a message to headwall unit 66, patient support apparatus 20, and/or exercise device 62 (through headwall unit 66 or patient support apparatus 20) that includes the patient ID and/or other necessary information to allow any of those devices to forward the exercise data from exercise device 62 to the EMR server without further utilizing patient support apparatus server 96. In other words, server 96 may send patient ID and/or other data to patient support apparatus 20, headwall unit 66, and/or exercise device 62 to enable them to report the exercise data to the EMR server without requiring the patient support apparatus server 96 to act as an intermediary of that exercise data.

Although exercise device 62 has been described herein as including a plurality of accelerometers 118 to detect the movement of exercise device 62 between its extended and retracted positions, it will be understood that this may be modified in some embodiments. For example, in some embodiments, location transceivers 116 may be configured to repetitively determine the location of location transceiver 116d with a frequency sufficiently fast to be able to detect the movement of exercise device 62 between its extended and retracted positions. In other words, in some embodiments, location transceivers 116 are used to detect both the overall position of exercise device 62 vis-a-vis space volume 64 as well as the individual repetitions made by the patient when using the device 62. In such embodiments, accelerometers 118 and/or gyroscope 132 may be omitted. Still other variations are possible.

In some embodiments, when system 60 detects that exercise device 62 is no longer inside space volume 64, system 60 is further configured to automatically undo any of the aforementioned steps that are automatically taken when system 60 previously determined that exercise device 62 was positioned inside space volume. Thus, for example, in some embodiments, controllers 130*a*, *b*, and/or *c* automatically unpair themselves when exercise device 62 moves outside of space volume 64. As another example, patient support apparatus 20 and/or headwall unit 66 may automatically send a message to patient support apparatus server 96, and/or another server, instructing the server that exercise device 62 is positioned outside of space volume 64. The message may include an instruction to disassociate that particular exercise device 62 with a particular patient. Still other automatic actions are possible.

In some embodiments, exercise device 62 is configured to communicate with one or more mobile devices 144, either in addition to, or in lieu of, communication with patient support apparatus 20 and/or headwall unit 66. As was noted, such mobile device 144 include, but are not limited to, one or more smart phones, tablet computers, laptops, or other types of mobile electronic device 144. In some of these embodiments, an individual may need to manually pair exercise device 62 with the mobile device 144. Once paired, exercise device 62 is configured to share information with the paired device 144 about the exercises performed by the patient using exercise device 62. In this manner, the user of mobile device 144 can, for example, see the number of reps performed by the patient using exercise device 62 and/or any of the other data discussed above that may be generated by exercise device 62 and its onboard sensors.

In some embodiments, data transceiver 138 may be a WiFi transceiver, and/or exercise device 62 may be configured to include a WiFi transceiver in addition to data transceiver 138. In either embodiment, controller 130*d* may be configured to utilize the WiFi transceiver to communicate the exercise data gathered from its onboard sensors (e.g. sensor 118 and/or 132) directly to network 90 without using either patient support apparatus 20 or headwall unit 66 as a conduit for such information. In some of these embodiments, patient support apparatus 20 and/or headwall unit 66 may be configured to wireless transmit to exercise device 62 its unique ID, which can be used as a proxy for the current location of exercise device 62. This unique ID may be forwarded by exercise device 62 to a server on LAN 90 which contains a data table, or has access to a data table, that correlates the patient support apparatus ID and/or headwall unit ID to a particular location within the healthcare facility.

Figure 9:
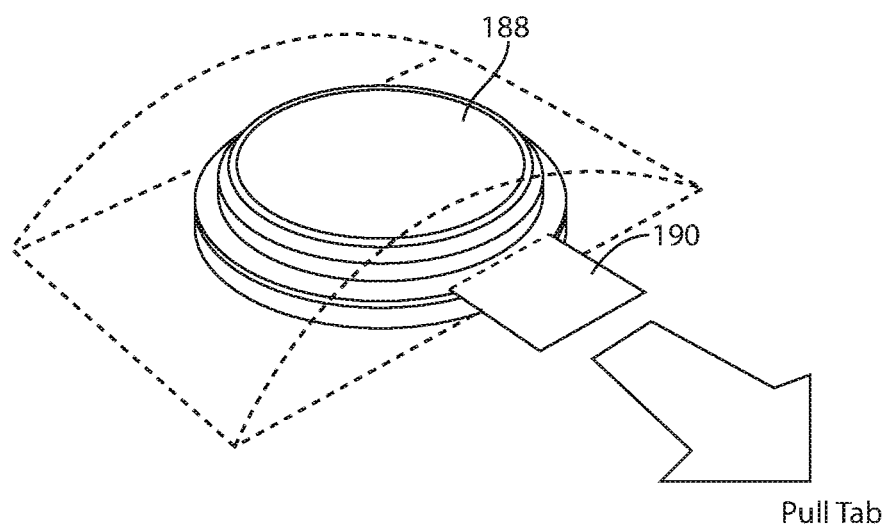
FIG. 9 is a perspective view of an electronics housing and pull tab that may be integrated into the exercise device, or another type of medical device.

In some embodiments, housing 188 includes a pull tab, such as the pull tab 190 shown in FIG. 9. In such embodiments, pull tab 190 includes a body sufficiently long to provide a temporary electrical insulation barrier between one or more batteries within housing 188 and the electronics housed therein. Thus, when pull tab 190 is in the position shown in FIG. 9, the battery or batteries are prevented from supplying electrical power to the electronic components within housing 188, thereby preserving the life of the battery. When exercise device 62, or another type of medical device 62, is to be used with a particular patient, the caregiver (or other authorized user) pulls pull tab 190 until it is removed from housing 188. This removal removes the electrical insulation between the battery and the conductors within housing 188 that are in electrical communication with the electronics stored therein, thereby providing power to those electronics. In some embodiments, controller 130*d* is configured to automatically start communicating with any in-range location transceivers 116 and/or perform the other functions described herein automatically upon receipt of power. Thus, in some embodiments, when a user removes pull tab 190, the electronics of exercise device 62 immediately begin operating to carry out the functions described herein, and there is no need for the user to take any additional steps. It will, of course, be understood that, either in lieu of, or in addition to, pull tab 190, exercise device 62 may include other structures, such as one or more switches, buttons, levers, motion-activated structures, or other structures that are manipulated by a user when he or she desires to start the operation of the electronics of exercise device 62.

In some embodiments, in order to extend the life of a battery, exercise device 62 may include circuitry (and/or controller 130*d* may be configured) to automatically enter a reduced power mode after a certain amount of time of non-use of exercise device 62. Once such a power-saving mode has been entered, controller 130*d* and/or internal circuitry within exercise device 62 may wait for a user to manually press a button, or take some other physical action, to cause exercise device 62 to exit the power-saving mode and return to its normal operating mode. Still other manners for conserving the battery life may be utilized.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. An exercise device for use with a patient while the patient is positioned on a patient support apparatus, the exercise device comprising:
   a first connector adapted to be releasably coupled to a first location of patient support apparatus;
   a patient-contacting portion adapted to contact a portion of the patient's body;
   a first elastic portion positioned between the first connector and the patient-contacting portion, the first elastic portion adapted to allow the patient to move the patient-contacting portion from a first position to a second position;
   a sensor adapted to automatically detect movement of the patient-contacting portion between the first and second position;
   a first location transceiver adapted to communicate with a second location transceiver physically separated from the exercise device, wherein the first location transceiver is adapted to determine position information regarding a relative position of the first location transceiver to the second location transceiver; and
   a wireless transceiver adapted to transmit movement data derived from the sensor to a recipient device, wherein the first location transceiver is an ultra-wideband transceiver adapted to communicate with the second location transceiver via ultra-wideband signals.

2. The exercise device of claim 1 wherein the movement data includes a rep count corresponding to a number of times the patient moves the patient-contacting portion from the first position to the second position.

3. The exercise device of claim 1 further comprising a second connector adapted to be releasably coupled to a second location of the patient support apparatus, and a second elastic portion positioned between the second connector and the patient-contacting portion, wherein the second elastic portion is also adapted to allow the patient to move the patient-contacting portion from the first position to the second position.

4. The exercise device of claim 3 wherein the first and second connectors are adapted to releasably attach to first and second siderails of the patient support apparatus, the patient-contacting portion is a foot pad, the exercise device is adapted to allow the patient to perform leg extensions, the first and second elastic portions are adapted to provide resistance to the patient's legs moving the foot pad from the first position to the second position, and the sensor includes an accelerometer adapted to detect acceleration of the foot pad as it moves between the first and second positions.

5. The exercise device of claim 1 wherein the recipient device is a second wireless transceiver positioned onboard the patient support apparatus, the wireless transceiver and second wireless transceiver are Bluetooth transceivers; and the sensor includes a gyroscope.

6. An exercise system for a patient, the exercise system comprising:
   a patient support apparatus and an exercise device, wherein the exercise device comprises:
   (i) a patient-contacting portion adapted to contact a portion of the patient's body, the patient-contacting portion adapted to be resistively moved between a first position and a second position;
   (ii) a first location transceiver;
   (iii) a first wireless communication transceiver; and
   (iv) a sensor adapted to automatically detect movement of the patient-contacting portion between the first and second positions;
   wherein the patient support apparatus comprises:
   (a) a support surface adapted to support a person;
   (b) a second location transceiver adapted to wirelessly communicate with the first location transceiver positioned on the exercise device;
   (c) a second wireless communication transceiver; and
   (d) a controller adapted to automatically pair the second wireless communication transceiver with the first wireless communication transceiver based on location information derived from communications between the first and second location transceivers, the automatic pairing taking place without requiring any manual instruction from a user regarding the first wireless communication transceiver, and wherein the first location transceiver is an ultra-wideband transceiver adapted to communicate with the second location transceiver via ultra-wideband signals.

7. An exercise system for a patient, the exercise system comprising:
   a patient support apparatus and an exercise device, wherein the exercise device comprises:
   (i) a first connector adapted to be releasably coupled to a first location of the patient support apparatus;
   (ii) a patient-contacting portion adapted to contact a portion of the patient's body, the patient-contacting portion adapted to be resistively moved between a first position and a second position;
   (iii) a first location transceiver; and
   (iv) a sensor adapted to automatically detect movement of the patient-contacting portion between the first and second positions;
   wherein the patient support apparatus comprises:
   (a) a support surface adapted to support a person;
   (b) a second location transceiver adapted to wirelessly communicate with the first location transceiver positioned on the exercise device, the second location transceiver adapted to generate a first location estimate of the first location transceiver, wherein the first location transceiver is an ultra-wideband transceiver adapted to communicate with the second location transceiver via ultra-wideband signals; and
   (c) a controller adapted to use the first location estimate to determine if the exercise device is currently coupled to the patient support apparatus or not, the controller further adapted to determine if the exercise device is currently coupled to the patient support apparatus by determining if the exercise device is currently within a volume of space.

8. The exercise system of claim 7 wherein the controller is further adapted to transmit a message to a remote server indicating that the exercise device is currently coupled to the patient support apparatus.

9. The exercise system of claim 7 wherein the patient support apparatus is further adapted to wirelessly receive movement data from the exercise device, wherein the movement data is derived from the sensor, the movement data includes a rep count corresponding to a number of times the patient moves the patient-contacting portion between the first and second positions, and the controller is further adapted to forward the movement data to a remote server.

10. The exercise system of claim 7 wherein the exercise device further comprises:
    a first elastic portion positioned between the first connector and the patient-contacting portion;
    a second connector adapted to be releasably coupled to a second location of the patient support apparatus; and
    a second elastic portion positioned between the second connector and the patient-contacting portion;
    wherein the first and second elastic portions are adapted to resist movement of the patient-contacting portion from the first position to the second position, and wherein the patient-contacting portion is a foot pad and the exercise device is adapted to allow the patient to perform leg extensions while seated on the patient support apparatus.

11. The exercise system of claim 7 further comprising a stationary unit mounted to a fixed location of a healthcare facility, the stationary unit comprising a third location transceiver adapted to wirelessly communicate with the first location transceiver positioned on the exercise device, the third location transceiver is adapted to generate a second location estimate of the first location transceiver and to forward the second location estimate to the controller, and wherein the controller is further adapted to use the second location estimate to determine if the exercise device is currently coupled to the patient support apparatus or not.

12. The exercise system of claim 7 wherein the patient support apparatus further comprises a third location transceiver adapted to wirelessly communicate with the first location transceiver positioned on the exercise device, the third location transceiver is adapted to generate a second location estimate of the first location transceiver, and to forward the second location estimate to the controller; and wherein the controller is further adapted to use the second location estimate to determine if the exercise device is currently coupled to the patient support apparatus or not.

13. The exercise system of claim 7 wherein the exercise device further includes a wireless transceiver adapted to transmit movement data derived from the sensor to a recipient device; wherein the recipient device is one of a smart phone, a tablet computer, a portable computer, or the patient support apparatus; and wherein the wireless transceiver is a Bluetooth transceiver.

14. The exercise system of claim 7 wherein the sensor includes an accelerometer adapted to detect acceleration of the patient-contacting portion as it moves between the first and second positions.

15. An exercise system for a patient, the exercise system comprising:
   a patient support apparatus and an exercise device, wherein the exercise device comprises:
   (i) a patient-contacting portion adapted to contact a portion of the patient's body, the patient-contacting portion adapted to be resistively moved between a first position and a second position;
   (ii) a first location transceiver;
   (iii) a sensor adapted to automatically detect movement of the patient-contacting portion between the first and second positions; and
   (iv) a first wireless communication transceiver adapted to wirelessly receive movement data from the exercise device, the movement data being derived from the sensor;
   wherein the patient support apparatus comprises:
   (a) a support surface adapted to support a person;
   (b) a second location transceiver adapted to wirelessly communicate with the first location transceiver positioned on the exercise device;
   (c) a second wireless communication transceiver;
   (d) a network transceiver adapted to communicate with a local area network of a healthcare facility; and
   (e) a controller adapted to automatically pair the second wireless communication transceiver with the first wireless communication transceiver based on location information derived from communications between the first and second location transceivers, the automatic pairing taking place without requiring any manual instruction from a user regarding the first wireless communication transceiver, wherein the controller is further adapted to forward the movement data to a remote server via the network transceiver, and to forward a first unique identifier corresponding to the patient support apparatus and a second unique identifier associated with a current location of the patient support apparatus to the remote server.

16. The exercise system of claim 15 wherein the movement data includes a rep count corresponding to a number of times the patient moves the patient-contacting portion between the first and second positions.

17. The exercise system of claim 15 wherein the exercise device further comprises:
   a first connector adapted to be releasably coupled to a first location of the patient support apparatus;
   a first elastic portion positioned between the first connector and the patient-contacting portion;
   a second connector adapted to be releasably coupled to a second location of the patient support apparatus; and
   a second elastic portion positioned between the second connector and the patient-contacting portion;
   wherein the first and second elastic portions are adapted to resist movement of the patient-contacting portion from the first position to the second position, and wherein the patient-contacting portion is a foot pad and the exercise device is adapted to allow the patient to perform leg extensions while seated on the patient support apparatus.

18. The exercise system of claim 15 further comprising a stationary unit mounted to a fixed location of the healthcare facility, the stationary unit comprising a third location transceiver adapted to wirelessly communicate with the first location transceiver positioned on the exercise device, and wherein the controller is further adapted to use information derived from communications between the third location transceiver and the first location transceiver to automatically pair the second wireless communication transceiver with the first wireless communication transceiver.

19. The exercise system of claim 15 wherein the patient support apparatus further comprises a third location transceiver adapted to wirelessly communicate with the first location transceiver positioned on the exercise device, and wherein the controller is further adapted to use information derived from communications between the third location transceiver and the first location transceiver to automatically pair the second wireless communication transceiver with the first wireless communication transceiver.

20. The exercise system of claim 6 wherein the first and second wireless communication transceivers are both Bluetooth transceivers, and the sensor includes a gyroscope and an accelerometer, wherein the accelerometer is adapted to detect acceleration of the patient-contacting portion as it moves between the first and second positions.

* * * * *